United States Patent
Suorsa et al.

(10) Patent No.: US 9,460,948 B2
(45) Date of Patent: Oct. 4, 2016

(54) DATA MANAGEMENT

(75) Inventors: Peter A. Suorsa, Amesbury, MA (US);
John B. Holz, Natick, MA (US);
Joseph D. Roth, Springboro, OH (US)

(73) Assignee: NCR Corporation, Duluth, GA (US)

( * ) Notice: Subject to any disclaimer, the term of this patent is extended or adjusted under 35 U.S.C. 154(b) by 1745 days.

(21) Appl. No.: 11/961,182

(22) Filed: Dec. 20, 2007

(65) Prior Publication Data

US 2009/0057421 A1    Mar. 5, 2009

Related U.S. Application Data

(60) Provisional application No. 60/969,837, filed on Sep. 4, 2007.

(51) Int. Cl.
| | | |
|---|---|---|
| *G06K 7/14* | (2006.01) | |
| *G06Q 50/22* | (2012.01) | |
| *G06Q 10/08* | (2012.01) | |
| *B65D 75/32* | (2006.01) | |
| *B41J 2/44* | (2006.01) | |
| *H01L 21/67* | (2006.01) | |

(52) U.S. Cl.
CPC .......... *H01L 21/67242* (2013.01); *B41J 2/442* (2013.01); *B65D 75/327* (2013.01); *G06K 7/14* (2013.01); *G06Q 10/08* (2013.01); *G06Q 50/22* (2013.01); *B65D 2203/00* (2013.01)

(58) Field of Classification Search
CPC .. B65D 75/327; B65D 2203/00; B41J 2/442; G06K 7/14; G06Q 10/08; G06Q 50/22; H01L 21/67242
See application file for complete search history.

(56) References Cited

U.S. PATENT DOCUMENTS

| | | | | |
|---|---|---|---|---|
| 4,078,660 | A * | 3/1978 | Lerro | 206/530 |
| 4,850,488 | A * | 7/1989 | Humbert | B65D 75/36 |
| | | | | 206/459.5 |
| 4,972,657 | A | 11/1990 | McKee | |
| 5,175,425 | A * | 12/1992 | Spratte | G06K 1/126 |
| | | | | 235/462.16 |
| 5,247,154 | A * | 9/1993 | Ahmed | G01N 21/84 |
| | | | | 219/121.83 |
| 5,700,998 | A * | 12/1997 | Palti | A61J 3/007 |
| | | | | 235/375 |
| 5,950,838 | A * | 9/1999 | Fletcher et al. | 206/775 |
| 5,992,742 | A * | 11/1999 | Sullivan et al. | 235/462.01 |
| 6,003,006 | A * | 12/1999 | Colella et al. | 705/2 |
| 6,003,773 | A * | 12/1999 | Durbin | G06K 7/10801 |
| | | | | 235/462.11 |
| 6,075,223 | A * | 6/2000 | Harrison | B41M 5/262 |
| | | | | 219/121.85 |
| 6,709,720 | B2 * | 3/2004 | Hayakawa | B23K 26/12 |
| | | | | 216/94 |
| 6,776,341 | B1 * | 8/2004 | Sullivan et al. | 235/462.01 |
| 6,824,061 | B1 * | 11/2004 | Hattersley et al. | 235/472.01 |
| 6,851,615 | B2 | 2/2005 | Jones | |
| 6,945,017 | B1 * | 9/2005 | Bonney et al. | 53/477 |
| 7,166,154 | B2 * | 1/2007 | Barreto | 106/31.13 |
| 7,370,797 | B1 * | 5/2008 | Sullivan et al. | 235/462.01 |
| 7,451,876 | B2 * | 11/2008 | Bossi et al. | 206/534 |
| 7,800,302 | B2 * | 9/2010 | Choi et al. | 313/509 |
| 7,918,402 | B2 * | 4/2011 | Conlon et al. | 235/491 |
| 7,926,730 | B2 * | 4/2011 | Auslander et al. | 235/494 |
| 8,020,702 | B2 * | 9/2011 | Strub et al. | 206/531 |

(Continued)

*Primary Examiner* — Daniel Walsh
(74) *Attorney, Agent, or Firm* — Schwegman, Lundberg & Woessner

(57) ABSTRACT

A package is provided for use with a track-and-trace data management system. The package comprises a base defining a plurality of compartments, each compartment containing an item, and a cover enclosing the compartments to retain each item inside a respective compartment. Each item carries a unique item code, and the package includes at least one unique security code. The relationship between the unique item code and the at least one unique security code is maintained by the data management system.

3 Claims, 10 Drawing Sheets

(56) References Cited

U.S. PATENT DOCUMENTS

| | | | |
|---|---|---|---|
| 8,038,008 B2* | 10/2011 | Bitner | 206/536 |
| 8,413,813 B2* | 4/2013 | Grosskopf | 206/531 |
| 8,644,982 B2* | 2/2014 | Greyshock et al. | 700/216 |
| 8,713,897 B2* | 5/2014 | Luciano et al. | 53/411 |
| 8,722,575 B2* | 5/2014 | Masciambruni | B41M 3/005 206/459.1 |
| 2001/0003167 A1* | 6/2001 | Iwakiri | H01L 21/67282 700/121 |
| 2001/0020594 A1* | 9/2001 | Hicks et al. | 206/459.5 |
| 2001/0041968 A1* | 11/2001 | Hamilton | 702/128 |
| 2002/0104773 A1* | 8/2002 | Kalvelage | B65D 43/0212 206/538 |
| 2003/0205621 A1* | 11/2003 | Soni et al. | 235/468 |
| 2005/0008875 A1* | 1/2005 | Taketomi et al. | 428/426 |
| 2005/0061706 A1* | 3/2005 | Reynolds et al. | 206/540 |
| 2005/0099476 A1* | 5/2005 | Chinea et al. | 347/100 |
| 2005/0237222 A1* | 10/2005 | Bogash | A61J 1/035 340/870.07 |
| 2005/0256830 A1* | 11/2005 | Siegel | G06F 19/3462 |
| 2005/0261344 A1* | 11/2005 | Jones et al. | 514/320 |
| 2006/0011504 A1* | 1/2006 | Gosebruch et al. | 206/459.5 |
| 2006/0065670 A1* | 3/2006 | Doublet et al. | 221/1 |
| 2006/0079996 A1* | 4/2006 | Benouali | 700/244 |
| 2006/0091208 A1* | 5/2006 | He et al. | 235/385 |
| 2006/0144749 A1* | 7/2006 | Arnold et al. | 206/538 |
| 2006/0173896 A1* | 8/2006 | Lyon | G06Q 10/08 |
| 2006/0255132 A1* | 11/2006 | Ortiz et al. | 235/383 |
| 2006/0260973 A1* | 11/2006 | Macinnes et al. | 206/528 |
| 2006/0261607 A1* | 11/2006 | Kromkowski | G09F 3/0352 292/315 |
| 2007/0048365 A1* | 3/2007 | Rao | 424/451 |
| 2007/0051072 A1* | 3/2007 | Lai | 53/411 |
| 2007/0105229 A1* | 5/2007 | Burns et al. | 436/56 |
| 2007/0119949 A1* | 5/2007 | Hattersley et al. | 235/472.01 |
| 2007/0119950 A1* | 5/2007 | Auslander et al. | 235/486 |
| 2007/0119951 A1* | 5/2007 | Auslander et al. | 235/491 |
| 2007/0125844 A1* | 6/2007 | Libin et al. | 235/380 |
| 2007/0131774 A1* | 6/2007 | Celestini | 235/462.45 |
| 2007/0185615 A1* | 8/2007 | Bossi | G06F 19/3462 700/244 |
| 2007/0200001 A1* | 8/2007 | Pinchen et al. | 235/487 |
| 2007/0210164 A1* | 9/2007 | Conlon et al. | 235/462.01 |
| 2007/0222556 A1* | 9/2007 | Robbins | B41J 3/01 340/5.9 |
| 2007/0235366 A1* | 10/2007 | Desai | B65D 75/327 206/531 |
| 2007/0265729 A1* | 11/2007 | Braun et al. | 700/215 |
| 2008/0000979 A1* | 1/2008 | Poisner | 235/462.01 |
| 2008/0035520 A1* | 2/2008 | Caracciolo | G06F 19/3462 206/531 |
| 2008/0097143 A1* | 4/2008 | Califorrniaa | 600/22 |
| 2008/0129037 A1* | 6/2008 | Roth et al. | 283/85 |
| 2008/0290168 A1* | 11/2008 | Sullivan | G06K 17/00 235/462.01 |
| 2009/0051027 A1* | 2/2009 | Lin | H01L 23/3157 257/734 |
| 2009/0057185 A1* | 3/2009 | Gelardi | A61J 1/035 206/532 |
| 2009/0059214 A1* | 3/2009 | Ackley et al. | 356/237.1 |
| 2009/0121472 A1* | 5/2009 | Battis | B41M 3/14 283/85 |
| 2009/0139893 A1* | 6/2009 | McGonagle et al. | 206/531 |
| 2009/0259486 A1* | 10/2009 | Burg | G06F 19/3418 705/2 |
| 2009/0297448 A1* | 12/2009 | Yan et al. | 424/9.1 |
| 2009/0302029 A1* | 12/2009 | Krishna et al. | 219/678 |
| 2010/0000899 A1* | 1/2010 | Burg | B65D 83/0463 206/459.1 |
| 2010/0294927 A1* | 11/2010 | Nelson et al. | 250/307 |
| 2010/0308061 A1* | 12/2010 | Loulourgas | B65D 81/3869 220/592.2 |
| 2011/0008527 A1* | 1/2011 | Teggatz et al. | 427/2.23 |
| 2011/0077771 A1* | 3/2011 | Greyshock et al. | 700/232 |
| 2011/0091068 A1* | 4/2011 | Stuck et al. | 382/103 |
| 2011/0186629 A1* | 8/2011 | Stuck et al. | 235/380 |
| 2011/0217487 A1* | 9/2011 | Masciambruni | G01K 1/14 428/29 |
| 2013/0014648 A1* | 1/2013 | Rognon et al. | 99/280 |
| 2013/0046594 A1* | 2/2013 | Davidson | 705/14.4 |
| 2013/0168270 A1* | 7/2013 | Koizumi et al. | 206/204 |
| 2013/0173484 A1* | 7/2013 | Wesby | G06Q 30/06 705/318 |
| 2013/0200999 A1* | 8/2013 | Spodak et al. | 340/5.65 |
| 2014/0034535 A1* | 2/2014 | Greyshock et al. | 206/438 |
| 2014/0074496 A1* | 3/2014 | Tsai | G06F 19/3462 705/2 |
| 2014/0214438 A1* | 7/2014 | Ahmadi | A61J 1/035 705/2 |
| 2014/0273246 A1* | 9/2014 | Bisso | G07D 7/0026 436/56 |

* cited by examiner

DATA MANAGEMENT

CROSS REFERENCE TO RELATED APPLICATIONS

This application claims priority to U.S. Provisional Application No. 60/969,837 entitled "Data Management" and filed on Sep. 4, 2007, the entire contents of which are hereby incorporated by reference herein.

BACKGROUND

There are many applications that involve managing a vast amount of data. One particular area involves tracing pharmaceuticals through a supply chain from manufacture through delivery to the end user. Given the prevalence of counterfeiting, and the health risks associated with counterfeit medications, tracing pharmaceuticals through a supply or distribution chain has now assumed added importance. In addition to such track and trace applications, data management may also be required for authentication of items containing security features, even if the items are not being tracked.

Track-and-trace functionality can be implemented by adding a security feature to the packaging of pharmaceuticals. However, this only allows the package to be traced and authenticated, not individual pharmaceuticals within the package.

Conventionally, many pharmaceuticals are shipped in bulk and then re-packaged at a pharmacy or other distribution center (e.g., factory, mail-order facility, and the like), either manually or by using a robotic dispenser. In this scenario, marking of an individual pharmaceutical (that is, a unit dose) for track-and-trace requires the use of a part, tag or other indicator that has been approved as an ingestible by the Food and Drug Administration (FDA). Obtaining such approval is difficult and expensive, requiring large-scale toxicology testing.

It would be advantageous to be able to use parts that have already been approved by the FDA to implement track-and-trace at the individual pharmaceutical (that is, unit dose) level.

SUMMARY

According to a first aspect of the invention there is provided a package comprising: a base defining a plurality of compartments, each compartment containing an item; and a cover enclosing each of the compartments to retain each item inside a respective compartment, wherein each item includes or otherwise carries a unique item code and the package includes or otherwise carries at least one unique security code, and where the relationship between each unique item code and the at least one unique security code is maintained by a database.

The items may comprise pharmaceuticals.

The package cover may comprise a frangible cover, such as is commonly used in a blister pack, for example a foil sheet.

The package may include a unique security code associated with each compartment. The code may be located within the compartment (for example, on an inside surface of the cover or on an inside surface of the compartment), or outside the compartment (for example, on an outside surface of the cover or on an outside surface of the compartment). The code may be applied by any suitable mechanism, for example, printing, application of a label, or the like. Where a unique security code is associated with each compartment, a database can be used to validate every pharmaceutical in the package, thereby enabling unit level track-and-trace for pharmaceuticals.

The unique security code is preferably machine-readable. The unique item code may also be machine-readable.

The unique item code carried by each item may be created by a laser beam. For example, the system provided by Datalase (trade mark) of Unit 3, Wheldon Road, Widnes, Cheshire, WA8 8FW may be used to write a unique barcode (such as a 2D barcode) on each item. Such a barcode may include information relation to the manufacturer, the place of manufacture, the type of pharmaceutical, the typical dosage, an expiry date, a unique serial number, and the like.

The unique item code may include the name of a pharmaceutical, dosage information, a unique serial number, and the like. For items other than pharmaceuticals, the unique item code may include any similarly identifying and/or other convenient information. Depending on the embodiment, the unique item code may be the same for a particular type of item (e.g., a particular pharmaceutical), and/or it may differ with individual instances of the item (e.g., with each pill of a particular pharmaceutical).

The base may comprise a plastic, such as a plastic approved by the FDA for use with pharmaceuticals.

The base may be optically transparent to allow a reader to read the unique item code and the associated unique security code by aligning the reader with a compartment.

The two codes (the item code and the security code) may be read simultaneously, nearly simultaneously, or sequentially.

Each item may have its respective item code created prior or subsequent to enclosure of that item in the package. If an item has its item code created subsequent to enclosure in the package, then a low power carbon dioxide laser may be used to write through a plastic base material.

The unique security code may comprise a luminophore, such as a silica matrix enclosing: a lanthanide, a dye, a quantum dot, or the like. As used herein, a luminophore is an atom or atomic grouping in a chemical compound, or part of a molecular entity, that manifests luminescence or, in some embodiments, more particularly, photoluminescence.

The unique security code may be provided by a covert ink. Where a covert ink is used, the code may be implemented as an invisible barcode, for example, photoluminescing in the near infra-red region of the electromagnetic spectrum.

The unique security code may comprise a barcode (such as a 2D barcode).

In a preferred embodiment, each item is marked with a DataLase (trade mark) Pharmamark (trade mark) coating.

In a preferred embodiment, each compartment is conformably molded around an item, so that the item does not move substantially during transport.

By virtue of this aspect of the invention, it is possible to implement track-and-trace of individual pharmaceuticals using substances that have already been approved by the FDA.

According to a second aspect of the present invention there is provided a data management system comprising: a data store for storing at least one entry, the entry including (i) information associated with an item in a multi-compartment package, and (ii) information about a security feature associated with that item; an authenticator operable to access the data store in response to a request from a remote reader and including (i) a reader validator to authenticate the remote reader, and (ii) a security feature validator to authenticate a security feature read by the remote reader and also operable to issue an authenticity confirmation in the event that a security feature is successfully validated; and a port for coupling the remote reader and the authenticator to enable requests to be transmitted from the remote reader to the authenticator and responses to be transmitted from the authenticator to the remote reader.

The data management system may also include a security gateway in communication with the port to protect the port against unauthorized access.

The term "data store" is used herein in a generic sense, and is intended to cover databases and other computing structures organized and arranged for storing and providing access to data.

The at least one data store entry may further include (iii) information about remote readers permitted to request authentication of that item. This information may be included directly in an entry or by a reference to another entry. This information may include the identity and location of remote readers permitted to request authentication of that item.

The identity and location of remote readers may be added to the item's data store entry (either directly or by a reference link) each time the item is authenticated. This enables the data management system to support a track and trace function. This allows an authorized user of the data store to ascertain where and when each item has been authenticated.

The information about remote readers permitted to request authentication of an item may be stored in a separate data store and linked to the appropriate entry for that item. The data store may comprise multiple data storage nodes (for example, organized in a cluster).

The data management system may be implemented as a cluster and may include a plurality of data stores, and have a plurality of authenticators (each an authentication node).

The identity information may include information about a hardware component within the remote reader, for example, a MAC address of a network connection (such as an Ethernet adapter); alternatively, the identity information may be a pre-assigned code unique to each remote reader.

The information associated with an item may include a description of the item, a serial number of the item, a place of manufacture of the item, and such like. Where the item includes a barcode, the information associated with the item may include the information stored by the barcode (either in full form or as a hash for computational speed and storage efficiency). Where a UPC (Universal Product Code) barcode symbology is used (e.g., UPC-A/UCC-12), the UCC (Uniform Code Counsel) Company Prefix from the barcode may be stored in the item's data store entry. Likewise, the Item Reference from such a barcode may be stored in the item's data store entry. In such case the UCC Company Prefix and/or Item Reference may be used as the unique index to access the appropriate entry from the data store. This is particularly useful in embodiments where all items recorded in the data store have associated barcodes.

The information associated with the item may include a global identification in addition, or as an alternative, to the UCC Company Prefix and/or Item Reference. A global identification is useful if there are customers who do not use barcodes to label items; for example, if a small item, such as a pharmaceutical is tagged with a security feature.

The information about a security feature associated with that item may include a representation of a unique spectral signature. The representation may be a series of pairs of numbers (e.g., one number relating to wavelength (or frequency), the other number relating to intensity or rate of change of intensity of emission at that wavelength), a unique code representing the spectral signature, or such like. Thus, the data store may store raw wavelength versus intensity data for a security feature, or a representation of this raw data. The unique spectral signature may be processed, for example, using algorithms, to derive a unique code or to transform the spectral signature to raw intensity and wavelength data. Alternatively, where a non-luminescent security feature is used, for example, RFID, the information may include unique data associated with that security feature.

As used herein, a spectral signature refers to aspects of luminescence from a security feature or group of security features that are unique to that feature or group of features. These aspects may include one or more of: presence or absence of emission at one or more wavelengths; presence or absence of a peak in emission at one or more wavelengths; the number of emission peaks within all or a portion of the electromagnetic spectrum comprising, for example, ultraviolet radiation to infrared radiation (e.g., approximately 10 nm to 1 mm); rate of change of emission versus wavelength, and additional derivatives thereof; rate of change of emission versus time, and additional derivatives thereof; absolute or relative intensity of emission at one or more wavelengths; ratio of an intensity of one emission peak to an intensity of another emission peak or other emission peaks; the shape of an emission peak; the width of an emission peak; or such like.

The information about a security feature associated with that item may include information about the entity to which the unique spectral signature is assigned. This may include the name of the entity (for example, a company name, a government name, a name of an authorized issuing body, or such like) to which the spectral signature is assigned, or a code referencing the name of the entity.

The information about a security feature associated with that item may include information indicating the type of security feature used, (for example, lanthanide-doped silica, a dye, quantum dots, RFID, and such like).

The security feature may be a luminophore, such as a silica matrix enclosing: a lanthanide, a dye, a quantum dot, or the like. As used herein, a luminophore is an atom or atomic grouping in a chemical compound, or part of a molecular entity, that manifests luminescence.

In typical embodiments, the security feature validator may be implemented in software.

The security feature validator may implement algorithms for transforming the unique spectral signature and/or transforming data received from the remote reader.

The security feature validator may authenticate a security feature read by the remote reader by processing data transmitted by the remote reader and comparing the processed transmitted data with the data store entry for that item. In particular, the security feature validator may compare the processed transmitted data with the stored information about a security feature associated with that item.

The reader validator may authenticate the remote reader by validating the identity of the remote reader, for example, by verifying that the remote reader has used the appropriate encryption key and protocols to access the data management system, and/or by verifying that the remote reader is listed as a permitted remote reader in the data store (either directly or by a reference to another data store).

The authenticity confirmation may comprise the following fields: a customer identification field (comprising a global identification and/or the UCC Company Prefix), a reader identity field, a request successful field, a unique system identification field, a timestamp field, and a unique transaction identifier field.

The unique system identification field may be populated by a unique number stored in firmware at the data management system. This unique number may be a pre-stored number assigned by the owner of the data store, a number associated with a hardware component, such as a MAC address of a network adapter of the system, or such like. This unique number may be added to each authenticity confirmation that is issued to allow the remote reader that requested authentication of a security feature to confirm the identity of the data management system (that is, the remote reader can use the unique system identification to authenticate the data management system).

The data management system may implement a timestamp by maintaining a timer using an offset from a known base, incremented by ticks based on a clock signal. The data management system may populate the timestamp field with the current value of the timestamp when the authenticity confirmation is being prepared.

A remote reader may store a timestamp from the last authenticity confirmation received to ensure that a timestamp received from a current authenticity confirmation is later than the stored timestamp. By applying a timestamp to each authenticity confirmation, and ensuring that a subsequent authenticity confirmation has a later timestamp than the previous authenticity confirmation, replay attacks can be avoided, or at least greatly reduced.

An authentication request having the same customer identification, remote reader identification, and timestamp automatically causes the authentication request to fail because it is treated as a replay attack.

The authenticator may increment a transaction identifier counter after each authenticity confirmation, thereby providing additional security against replay attacks.

An authenticity confirmation may be in the form of a certificate of authenticity that can be transmitted to and automatically processed by other computer systems, in a similar way to how a public key encryption certificate is provided by Web sites.

The authenticator may be operable to update a customer's entry (or to add sub-entries thereto) for an item to indicate each occasion on which that item is validated by the data management system. The authenticator may also update the customer's entry for an item to include the location of the remote reader that requested authorization of the customer's item. The data management system may populate a separate tracking data store (referenced by the customer's entry) that can be used to provide track and trace information. The decision on whether to use a separate data store or not is based on the preferences of the owner of the data management system.

The authenticator may be operable to create a log file for each authentication failure. The authenticator may include an exception condition that triggers a notification process in the event of an authentication failure. The notification process may inform the owner of the data store and/or the customer associated with the item about the failure to authenticate. The notification process may include details about whether the remote reader was authorized and whether the security feature was authorized.

The port may include a customer interface to allow the customer to send requests to the data store. The customer interface may be a Web front end to a SQL database management system, or any other convenient interface to allow a customer to make pre-defined requests. Alternatively, the contents of the data store may be mirrored (or otherwise transferred) to a separate system (a customer request system), and the customer request system may include a customer interface to allow the customer to send requests relating to the transferred data. This has the advantage of removing a potential security risk by having a customer interface in the data management system. The customer request system may be implemented by a query database.

The data management system may allow a customer to request a list of all authentications requested by readers, including any authentication requests that were not successful.

The port may comprise a plurality of different logical and/or physical connections. The port may implement Web technologies, and be accessible through a Web connection.

The security gateway may include one or more conventional firewalls (for example, based on proxy servers) and conventional load balancers. The firewalls scan incoming requests to ensure that no viruses or worms are present, and to ensure that the system is not probed. As firewalls and load balancers are well known to those of skill in the art, they will not be described in detail herein.

The authenticator may include a parameter issuing object that issues parameters to a remote reader to instruct the remote reader about what parameters to apply when reading the security feature and/or processing data read from the security feature. The parameter issuing object may issue a reader control command having a data structure comprising: a customer identification field (comprising a global identification and/or the UCC Company Prefix), a reader identity field, an algorithm identification field (referencing an algorithm stored by the remote reader), algorithm parameter fields (including any parameters needed by the referenced algorithm), a unique system identification field, a timestamp field, and a unique transaction identifier field. The parameter issuing object may be used to control the remote readers and make it more difficult to simulate the response of a security feature.

A request from a remote reader may be stored in non-volatile memory and then erased when actioned by an authenticator node (either by issuing an authenticity confirmation if validated, or by responding with a failure message if not validated); thereby ensuring a response is issued, even if a node fails. The failure message may include limited information, for example, it may not include the unique system identification field or any other details that may help a criminal to deduce information about the data management system.

By virtue of this aspect of the invention a highly secure data management system is provided that can be used for authenticating security features and also for track and trace applications.

According to a third aspect of the present invention there is provided a method of managing data, the method comprising: storing in a data store for each item in a multi-compartment package information (e.g., data) associated with (i) that item, and (ii) a security feature associated with that item; receiving a request from a remote reader where the request includes data read from a security feature and data read from an item associated with that security feature; processing the read data to derive an index for accessing a relevant entry in the data store; accessing the data store using the derived index; comparing the read data with stored data for that index; and generating an authenticity confirmation in response to a match.

The method may comprise the further step of authenticating the remote reader.

Additionally, the method may comprise the further step of processing the read data to derive data associated with the item and the associated security feature, and the step of comparing the derived data with stored data for the derived index in addition to, or in lieu, of the step of comparing the read data with stored data for the derived (re. "that") index.

The step of storing information (e.g., data) about an item may include storing information derived from reading a spatial code on the item, such as a barcode. Such information may include a customer number (e.g., a UCC Company Prefix), an item or product number (e.g., Item Reference), and the like, as provided for by one or more utilized barcode symbologies (e.g., UPC-A/UCC-12).

The step of authenticating the remote reader may include confirming that a unique number provided by the remote reader (the reader identification number) is associated with the customer number provided by the remote reader.

According to a fourth aspect of the present invention there is provided an authentication system for authenticating an item, the system comprising: a data management system according to the second aspect of the invention, and at least one remote reader coupled to the data management system, the remote reader comprising: (i) a security module, and (ii) a read engine for reading an item code carried by an item and a security code associated with that item code.

The security module may include an encryption unit. Additionally, the security module may be tamper responsive for destroying any stored encryption data (such as keys, algorithms, or such like) in the event that the security module is tampered with. Tamper responsive features typically detect any attempt to disassemble or penetrate a security module, for example, by detecting penetration of a conducting mesh surrounding the unit, by detecting removal of screws or other fixtures holding the unit together, or by detecting cutting of any data-carrying wires. Tamper responsive features are typically connected to an erase pin on a non-volatile memory storing encryption data.

The security module may include a unique identification, which may be conveyed to the data management system as part of an authentication request, to allow the remote reader to be identified by the data management system.

Prior to removing an individual item from the package, a consumer can validate the authenticity of the item using the authentication system. When the item code and associated security code are scanned by the reader, the data management system can create additional records that tie the identity of an item dispensed to the identity of the person to whom the item is dispensed. This allows any problems with lots or batches of pharmaceuticals to be matched directly to the consumers of those pharmaceuticals. Such a person may be identified through association with a unique reader used to scan the item and associated security code, and/or through entry of one or more of unique numeric, biometric, card scan or other information through use of one or more of a numeric keypad, biometric input device and/or card scanner associated with the reader, and the like According to a fifth aspect of the present invention there is provided a secure reader for reading a spatial code and a security feature, the secure reader comprising: (i) a security module, and (ii) a read engine for reading both an item code carried by an item, and a security code provided on a package for, or more preferably, containing that item.

The security module may be operable to transmit a unique reader identification each time an authentication request is sent to a remote data management system.

The security module may include an encryption unit. Additionally, the security module may be tamper responsive for destroying any stored encryption data (such as keys, algorithms, or such like) in the event that the security module is tampered with. Tamper responsive features typically detect any attempt to disassemble or penetrate a security module, for example, by detecting penetration of a conducting mesh surrounding the unit, by detecting removal of screws or other fixtures holding the unit together, or by detecting cutting of any data-carrying wires. Tamper responsive features are typically connected to an erase pin on a non-volatile memory storing encryption data.

The security module may include a unique identification, which may be conveyed to the data management system as part of an authentication request, to allow the remote reader to be identified by the data management system.

The security module may store a plurality of controlling and/or processing algorithms which can be selectively used to read the security feature or to process data read from the security feature. The algorithms may have associated parameters stored by the security module, including read delay time (time delay between exciting a security feature and reading the luminescence emitted in response to that excitation, integration time, spectral range (that is, the wavelength range over which a luminescence spectrum is recorded), spectral resolution (that is, the number of discrete sample points read within a spectral range), and such like. The associated parameters may be incorporated (for example, hard coded) into the algorithms, or they may be stored separately from the algorithms, so that the data management system can transmit updated parameters to the secure reader for use with the algorithms already stored in the secure reader. The parameters may include reading parameters that control how the secure reader reads a security feature, and processing parameters that control how the secure reader processes data read from a security feature. The data management system may select a particular algorithm to be used by a secure reader on a scheduled or randomized basis.

The security module may include a clock generator, and may also include a timestamp generator.

The secure reader may include a global positioning system (GPS) receiver to allow the reader to provide the data management system with details of the reader's current position. In operation, the GPS receiver continually determines its position. Periodically, the data management system may send a packet request to the reader which asks for the reader's unique hardware identification ID (which may be a MAC address of a communications adapter), the current latitude/longitude, and a GPS timestamp and a timestamp from the timestamp generator.

The GPS timestamp may be used to calibrate the timestamp from the timestamp generator. If the times (which are incremented as ticks from a known base) do not match, then the secure reader may have been compromised.

The latitude and longitude (that is, the position of the secure reader) are determined from a GPS Course Acquisition (CA) signal, which has a current accuracy of 100 meters. As the CA accuracy increases with newer GPS receivers, the positional accuracy will also increase.

An altitude value may also be provided to indicate where in a building (what floor) the secure reader is located.

These periodic readings may be stored in the data store of the data management system. If there is a change in the readings without a corresponding re-registration request from the secure reader incorporating the GPS receiver, then the data management system may execute a trigger to notify the owner of the data management system. Such readings may be taken daily, although the frequency of such readings may depend on the service level requested and paid for by the customer.

In addition to periodic readings, the data management system may take readings during initial registration of a secure reader.

The secure reader may be operable to upload data from a security feature for storing with a data management system. The reader may use an association request having a data structure comprising: a customer identification field (comprising a global identification and/or the UCC Company Prefix), a reader identity field, a function request field indicating that the desired function is to store security feature data in the data store, a timestamp field, and spectral data fields. The spectral data fields may include the number of bytes of data to be sent, the spectral resolution, the number of points sampled, the actual spectral data (which may be sent as multiple packets of data), and such like.

The secure reader may be operable to read a plurality of spatial codes in a single operation and also to read a plurality of security features in a single operation, and to link each read spatial code with its corresponding security feature.

The secure reader may be operable to prepare and communicate a registration request to the remote data management system so that the data management system can register the secure reader as active.

The secure reader may include an auxiliary cryptographic device that enables the reader to be authenticated prior to allowing any software to be downloaded or updated. The auxiliary cryptographic device may be a dongle, a smart card, or the like.

The auxiliary cryptographic device may store a unique code that is transmitted to the remote data management system by the secure reader as part of the registration request. The secure reader may transmit a de-registration request to the remote data management system if the auxiliary cryptographic device is removed, or if the unique code is not provided by the auxiliary cryptographic device. If the auxiliary cryptographic device is replaced, then the secure reader may have to re-register with the remote data management system. The remote data management system may compare current information transmitted by the secure reader as part of the re-registration request with information transmitted prior to de-registering the auxiliary cryptographic device. This information may include location information in addition to information relating to the identity of the secure reader, for example, a MAC address and hardware serial numbers. If the current information is consistent with the information transmitted prior to de-registering the auxiliary cryptographic device then the data management system may re-register the secure reader.

The initial registration of a secure reader may compare information (except for location) that was recorded at the time of manufacture of that secure reader.

The read engine may include a first component for reading the item code carried by the item, and a second component for reading a security code provided on a package for or, more preferably, containing that item. The first and second components may be mounted for reading from only one side of the package. Alternatively, the first and second components may be mounted on opposing sides of a bifurcated reader so that the read engine may be used for reading opposing sides of the package.

According to a sixth aspect of the present invention there is provided a data management system for tracking an item, the system comprising: a data store for storing at least one entry, the entry including (i) information identifying an item, and (ii) information about a security feature associated with that item; an authenticator operable to access the data store in response to a request from a remote reader and including (i) a reader validator to authenticate the remote reader by ascertaining the identity and location of the remote reader, and (ii) a security feature validator to authenticate a security feature read by the remote reader and to issue an authenticity confirmation in the event that a security feature is successfully validated; a tracker for maintaining a record in the data store of each occasion on which the item is authenticated and the location of the remote reader that requested authentication of that item; and a port for coupling the remote reader and the authenticator to enable requests to be transmitted from the reader to the authenticator and responses to be transmitted from the authenticator to the reader.

The data management system may include a security gateway in communication with the port to protect the port against unauthorized access.

By virtue of this aspect of the invention, an item can be traced from manufacture through a supply chain or distribution chain, thereby providing authenticated track and trace functionality.

According to a seventh aspect of the invention there is provided a method for charging for secure data management and item authentication, the method comprising: charging an initiation fee to a customer to create an entry for an item owned or manufactured by the customer, charging an annual maintenance fee to maintain the entry for the customer; charging an authentication fee each time the customer requests authentication of the item.

The method may include the further step of charging a lease fee to a customer for each secure reader the customer leases, where a secure reader is required to request authentication of an item.

The method may include charging the customer on a per byte basis.

The method may include charging an additional fee to issue updated configuration parameters to secure readers to instruct the secure readers about how to operate.

The method may include charging the customer for a track and trace report for an item, the track and trace report being generated automatically and including details of when the item was authenticated, and the identity and location of secure readers that requested authentication of the items.

According to an eighth aspect of the invention there is provided a method of charging a customer for secure data management and item authentication, the method comprising: providing the customer with secure readers for reading security features applied to items, licensing a data management system to a customer for the customer's use, and charging a license fee based on the number of authentications performed in a specified time period.

The specified time period may be daily, weekly, monthly, quarterly, annually, or such like.

The method may include the step of charging a fee to the customer for securely populating the data management system with security feature information.

According to a ninth aspect of the invention there is provided a method of marking an item to allow validation and tracing of that item, the method comprising: providing a package having an optically transparent base defining a plurality of compartments; inserting individual items into each of the compartments; writing a unique item code on each item; and applying a unique security code in registration with each compartment, to allow association of the item code and the security code for each compartment.

In some embodiments, a method of marking items and packaging thereof is provided, the method comprising: providing a package having an optically transparent base defining a plurality of compartments; inserting an individual item into each of the plurality of compartments; applying a unique item code to each individual item; and applying a unique security code to each compartment. The method may comprise the further step of associating the unique item code for each individual item with the unique security code for the compartment into which the respective item is inserted. Depending on the embodiment, applying a unique item code to each individual item and/or a unique security code to each compartment may comprise writing, printing, etching, labelling, adhering, and the like, the unique item code and/or the unique security code to the respective item and/or compartment. Likewise, in some embodiments, the unique security code may be applied in registration with the unique item code to allow simultaneous or near simultaneous reading of the unique item code and the unique security code.

According to a tenth aspect of the invention there is provided a package comprising: a sealed container defining an optically transparent portion and including at least one unique security feature; and an item located within the container, and carrying a unique item code, where the item code is aligned with the optically transparent portion to facilitate reading of the item code from outside the package; wherein a remote database stores the relationship between the unique security feature and the unique item code to allow authentication of the item.

The item may be a pharmaceutical, a medical device (such as a stent, a pacemaker, a surgical instrument, or the like), an electronic component (such as a microprocessor, a resistor, or the like), a mechanical component (such as a brake pad) or the like.

An embodiment of the present invention will now be described, by way of example, with reference to the accompanying drawings.

DETAILED DESCRIPTION

Figure 1:
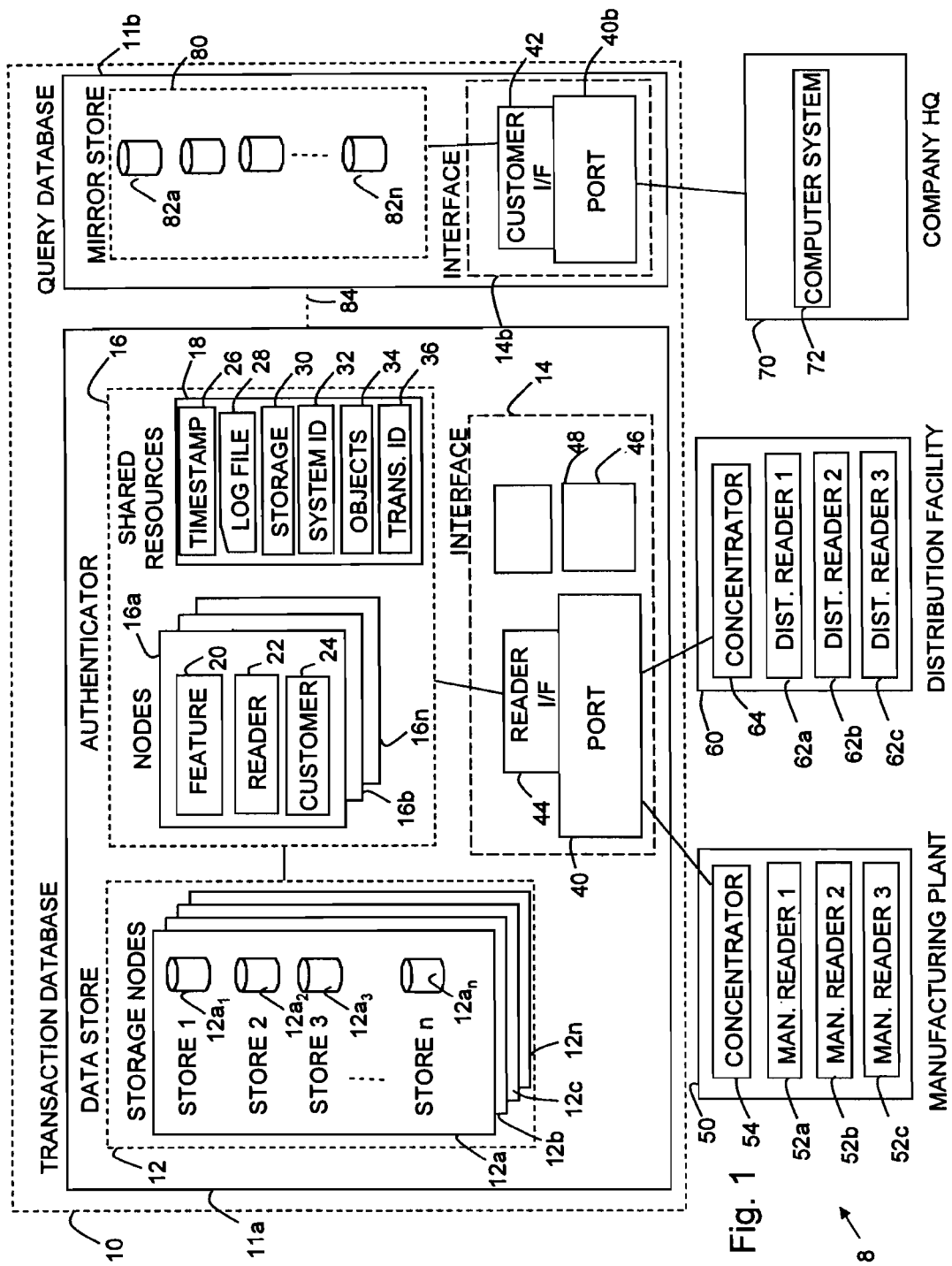
FIG. 1 is a block diagram illustrating a networked authentication system including a data management system according to one embodiment of the present invention.

Reference will now be made to FIG. 1, which is a networked authentication system 8 including a data management system 10 according to one embodiment of the present invention.

Structure of Networked Authentication System

The data management system 10 comprises a transaction database 11a selectively coupled to a query database 11b.

The transaction database 11a comprises: a data store 12 coupled to an interface 14 via an authenticator 16.

The data store 12 comprises a plurality of storage nodes 12a, 12b, . . . 12n, each storage node having a plurality of storage areas $12a_1, 12a_2, \ldots 12a_n$. Each storage area can store a large number of entries relating to items to be authenticated.

The authenticator 16 comprises a plurality of authenticator nodes 16a, 16b, . . . 16n (one of which will be referenced as $16_x$), each coupled to shared resources 18. Each authenticator node 16 includes a security feature authenticator 20, a secure reader authenticator 22, and a customer authenticator 24. The shared resources 18 include processes, files, data, objects, and hardware that are used by the authenticator nodes $16_x$. As shown in FIG. 1, the shared resources 18 comprise: a timestamp generator 26 continually incrementing from a known base, a log file 28 for recording any failed authentication attempts, non-volatile storage 30 for storing authentication requests until accessed and actioned by an authentication node $16_x$, a unique system identification 32 for identifying the data management system 10, an object repository 34 containing various objects accessible by the authentication nodes $16_x$, as will be described in more detail below, and a transaction identifier counter 36 that is incremented each time a successful authentication is performed by the security feature authenticator 20.

The interface 14 comprises: a port 40 supporting logical and physical connections to allow remote components to access the data management system 10, a reader interface 44 for allowing authorized remote readers to request authentication of a security feature read by the remote readers, a security gateway 46 implementing firewalls for securing the interface 14 against unauthorized access, and a load balancer 48 to optimize use of the authenticator nodes $16_x$.

The query database 11b comprises: an interface 14b including a port 40b (similar to port 40), and a customer interface 42. The port 40b includes a security gateway (not shown) implementing firewalls for securing the interface 14b against unauthorized access. The query database 11b also includes a store 80 including a plurality of storage areas (82a to 82n).

The query database 11b can periodically be coupled to the transaction database 11a (illustrated by broken line 84) to transfer some or all of the contents of the data store 12 from the transaction database 11a to the query database 11b. The customer interface 42 may be disconnected when this occurs to isolate the transaction database 11a from possible attacks through the customer interface 42.

The contents of the data store 12 are typically transferred from the transactional database 11a to the query database 11b using an extract, transform, and load command (ETL command). The transactional database 11a stores current data and is optimized for executing transactions (such as authentication requests); whereas, the query database 11b may store historical data to allow an owner or a customer to execute queries covering a long time period.

Once the required contents of the data store 12 have been transferred to the query database 11b, the customer interface 42 is re-connected to allow customers to access the query database 11b and run permitted queries against the stored data.

Figures 2A, 2B:
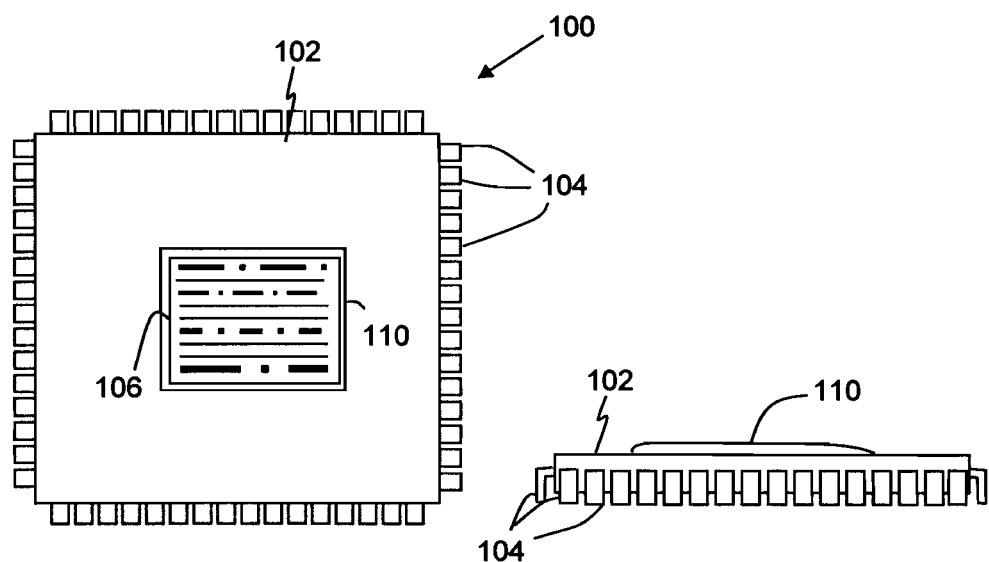
FIGS. 2A and 2B are schematic plan and elevation views respectively of a semiconductor microprocessor incorporating a security feature.

Reference will now also be made to FIGS. 2A and 2B, which are schematic plan (FIG. 2A) and elevation (FIG. 2B) views of a semiconductor microprocessor 100.

FIG. 1 illustrates three different facilities coupled to the data management system 10: a manufacturing plant 50 that makes semiconductor microprocessors 100 of the type shown in FIGS. 2A and 2B, a distribution facility 60 that receives the manufactured microprocessors 100 and ships them to customers, and a headquarters 70 of the company that designs and manufactures the microprocessors 100.

The manufacturing plant 50 includes a plurality of secure readers 52, only three of which are shown, each of which can connect to the reader interface 44 in the data management system 10 via a concentrator 54 within, or accessible from, the manufacturing plant 50. Similarly, the distribution facility 60 also includes a plurality of secure readers 62, again, only three of these are shown in FIG. 1, and each of which can connect to the reader interface 44 in the data management system 10 via a concentrator 64 in the distribution facility. The company headquarters 70 includes a computer system 72 having access to the customer interface 42 of the data management system 10.

The microprocessor 100 comprises a packaged component having an upper surface 102 surrounded on four sides by connector pins 104 (only a few of which are labelled) for allowing the microprocessor to be inserted into a motherboard socket. The upper surface 102 has a two-dimensional (2D) barcode 106 laser etched thereon. A security feature 110 (best seen in FIG. 2B) comprising lanthanide-doped silica particles suspended in an optically transparent ink is applied on top of, and in registration with, the 2D barcode 106. The security feature 110 acts as a security seal for the barcode, and can be read simultaneously (or near simultaneously) with the 2D barcode 106.

The lanthanide-doped silica particles can be fabricated using any convenient method. One way of making lanthanide-doped particles is described in US patent application number 2004/0262547, entitled "Security Labelling," and US patent application number 2005/0143249, entitled "Security Labels which are Difficult to Counterfeit", both of which are incorporated herein by reference.

Figure 3:
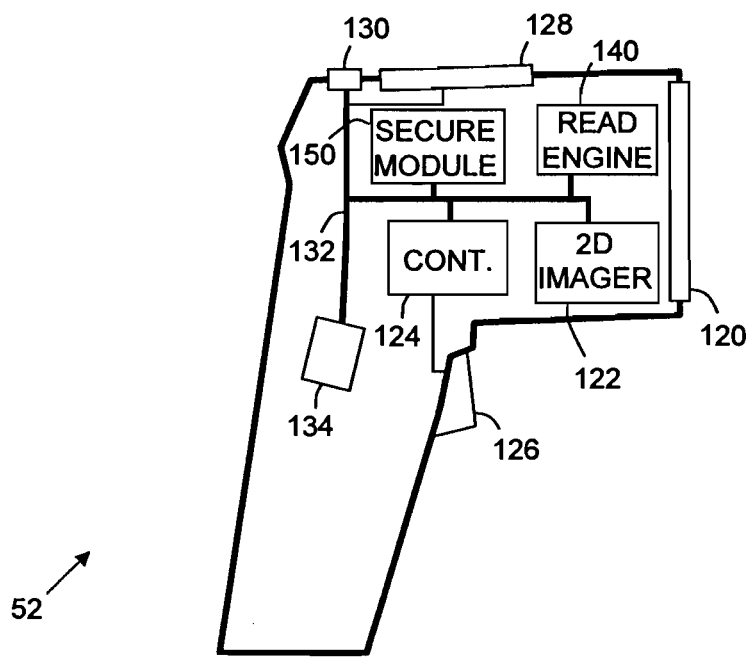
FIG. 3 is a schematic diagram of a part (a secure reader) of the networked authentication system of FIG. 1.
Figure 4:
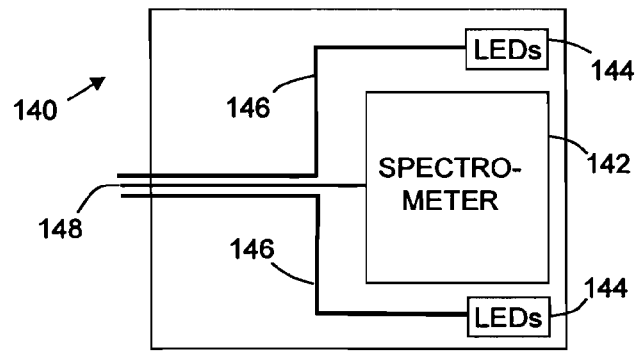
FIG. 4 is a block diagram of a part (a read engine) of the secure reader of FIG. 3.
Figure 5:
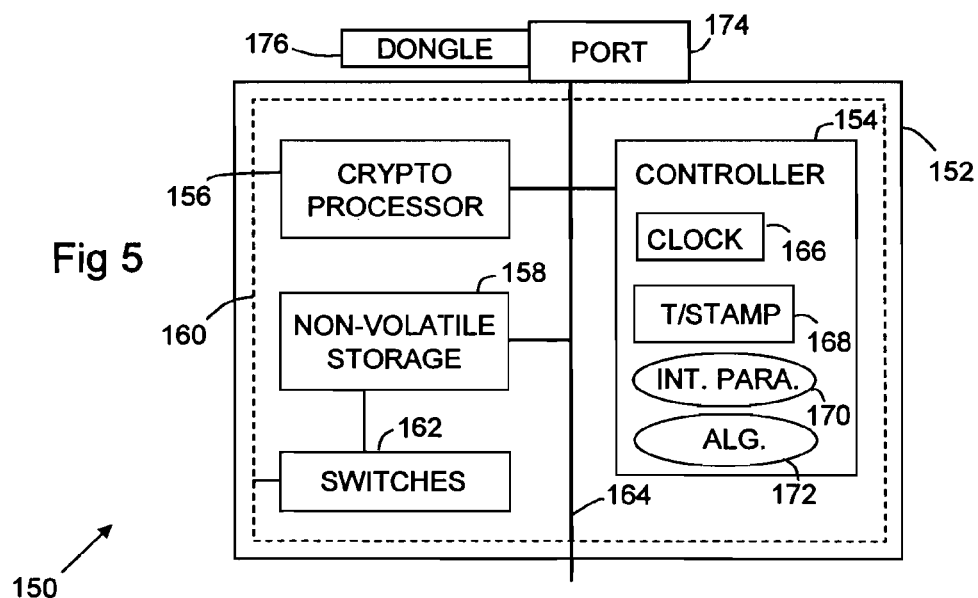
FIG. 5 is a block diagram of another part (a secure module) of the secure reader of FIG. 3.

Reference is now also made to FIG. 3, which is a schematic diagram of one of the (identical) secure manufacturing readers 52 shown in FIG. 1, and also to FIGS. 4 and 5, which are block diagrams showing parts of the secure reader 52 in more detail. Each secure reader 52 is located within the manufacturing plant 50 and connects to the data management system 10 via a concentrator 54 that handles the communications with the reader interface 44.

The secure reader 52 is a modified conventional 2D barcode scanner, such as those available from Symbol Technologies, Inc. (trade mark) or Metrologic Instruments, Inc. (trade mark). The secure reader 52 comprises: a scanning window 120; a conventional 2D barcode imager 122 aligned with the scanning window 120; associated control electronics 124 for activating the conventional imager 122 (in response to a user depressing a trigger 126) and processing data received from the imager 122; an LCD panel 128 for outputting information to the user (such as information from an item read by the scanner, the status of the scanner, and such like); a function button 130 for controlling the function of the secure reader 52; internal connections 132 for interconnecting the various components within the secure reader; a communications module 134 (including a unique hardware identification in the form of a MAC address) implementing a cable or wireless connection to the concentrator 54; a security feature read engine 140 for reading the security feature 110 carried by a microprocessor 100; and a security module 150 coupled to the security feature read engine 140.

The read engine 140 (best seen in FIG. 4, which is a block diagram illustrating the read engine 140 in more detail) includes a spectrometer 142 for detecting luminescence in the visible and near infra-red regions of the electromagnetic spectrum, and an excitation source 144 in the form of LEDs disposed on opposing sides of the spectrometer 142 and emitting in the ultra-violet region of the electromagnetic spectrum. The LEDs 144 are coupled to the security module 150 by power lines 146, and the spectrometer 142 is coupled to the security module 150 by power and data lines 148.

The security module 150 (best seen in FIG. 5, which is a block diagram illustrating the security module 150 in more detail) comprises a sealed housing 152 in which the following components are mounted: control electronics 154 for driving the security feature read engine 140 and for processing data received therefrom; a conventional cryptographic processor 156 to support encrypted communication with the concentrator 54; non-volatile storage 158 for storing encryption keys and/or encryption algorithms and the unique system identification 32 of the data management system 10; a security membrane 160 (illustrated by a broken line in FIG. 5) disposed around an inside surface of the housing 152 and coupled to tamper switches 162 that activate an erase line of the non-volatile storage 158 when the membrane 160 is penetrated or disturbed, thereby destroying any stored encryption data (such as keys, algorithms, or such like) in the event that the security module 150 is tampered with. An internal bus arrangement 164 is also provided to facilitate communications within the housing 152, and a communication adapter 166 is provided to facilitate communications between the security module 150 and the other components of the secure reader 52.

The control electronics 154 includes a clock 166, and a timestamp generator 168 that maintains a timer using an offset from a known base, incremented by ticks based on the clock 166. The control electronics 154 also accesses and executes from the non-volatile storage 158 interrogation parameters 170 and processing algorithms 172.

An externally-accessible port 174 is provided to allow an auxiliary cryptographic device 176 (a dongle) to be coupled to the secure module 150.

Referring again to FIG. 1, the distribution facility readers 62 are very similar to the manufacturing facility readers 52, the main difference being that the distribution facility readers 62 do not support entry creation mode, as will be explained in more detail below.

Operation of Networked Security System

Operation of the networked security system will now be described. There are four main operations that the networked security system can perform: (i) registration of remote readers 52, 62, (ii) association of security features with barcodes, (iii) authentication of items (such as the microprocessor 100), and (iv) control of the remote readers 52, 62 by downloading parameters from the data management system 10.

Prior to describing these operations, the general structure of an entry in the data store 12 will be described, with reference to FIG. 1 and FIG. 6, which is a diagram illustrating the data typically stored in an entry for an item.

Figure 6:
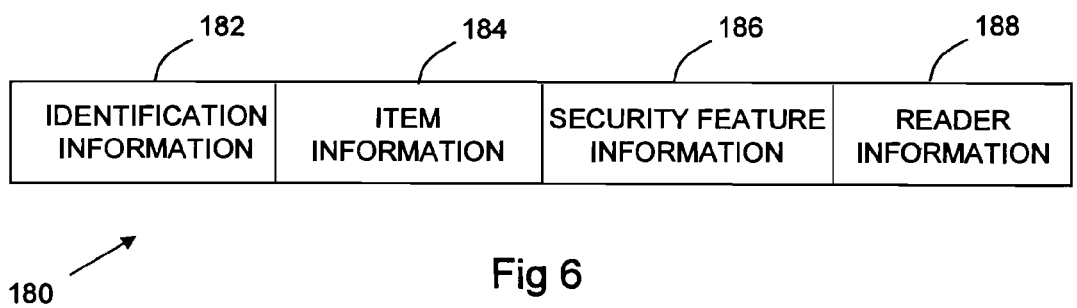
FIG. 6 is a diagram illustrating the data typically stored in an entry for an item in the data store of FIG. 1.

In FIG. 6, an entry 180 comprises four main categories of information: customer identification information 182, item information 184, security feature information 186, and remote reader information 188.

The customer identification information 182 includes fields for a global customer identification and for a UCC Company Prefix from a 2D barcode. The global customer identification is assigned by the owner of the data management system 10, and is unique for each customer. The customer identification information may include additional fields not listed herein.

The item information 184 includes fields for a description of the item (for example, a microprocessor), a serial number and/or part number of the item, a location where the item is manufactured and/or distributed, and information from a barcode on the item. Additional or different fields may be provided depending on the particular item, the application and/or industry that item will be used in, and the value of that item.

The security feature information 186 includes fields indicating the type of security feature (optical, magnetic, radio-frequency, or such like), and data representing the security feature. The data representing the security feature may be raw data, or some transformation of the raw data. In this embodiment, the security features used are optical, and the data representing the security feature is raw data stored in pairs of data points, namely, intensity and wavelength for each wavelength of interest. The security feature information 186 may be populated by the owner when a security feature 110 is assigned to a customer, or it may be populated by the customer uploading the security feature information using the readers 52.

The remote reader information 188 includes fields indicating the identity and/or location of those readers 52, 62 that are permitted to request authentication of that item (that is, the item listed in the entry 180). These fields may include that information directly, or they may provide a link to another storage area $12a_x$ or storage node $12x$ that stores such information. In this embodiment, the remote reader information 188 provides a link to a storage node $12x$ that stores the identity of those remote readers 52, 62 authorized to request authentication of that item. In this example, storage node 12c stores the remote reader identification information, and will be referred to herein as "the reader identification storage node 12c".

Remote Reader Registration

The first operation that will be described is registration of remote readers 52, 62. This operation will be described with reference to FIG. 7, which is a flowchart illustrating the steps involved in registering a remote reader 52, 62 with the data management system 10.

Initially, the manufacturer of the item (in this example, the microprocessor 100) requests the data management system owner (hereinafter, "the owner") to tag the microprocessor 100 (step 200). This involves the customer contracting with the owner to receive authentication services. In this example, this involves the customer paying an initialization fee to establish an entry 180 for each type of item (in this example, each model of microprocessor 100) to be authenticated, and an annual storage fee to pay for the data management system owner to store the customer's information. The owner will also sell or lease to the customer one or more remote readers 52 for the manufacturing plant 50, one or more remote readers 62 for the distribution facility 60, and dongle 176 for each reader 52,62.

The next step is for the owner to assign a unique global identification to the customer (step 202). The unique global identification is a unique number incremented by one for each new customer. The unique global identification is loaded by the owner into the non-volatile storage 158 of each reader 52, 62 sold or leased to that customer.

The next step (step 204) is to create a master entry in the data store 12 to allow the customer to populate entries under that master entry for the different models of microprocessors 100 to be authenticated. In this example, only one model of microprocessor is to be authenticated (and no other types of items are to be authenticated), so there will only be one entry for this customer. Each customer may have multiple entries, for example, a customer may have ten different models of microprocessors, and five different models of north bridge memory management controllers. In such an example, the customer would have fifteen different entries. Creation of a master entry does not restrict the number of entries that a customer may populate.

To create a master entry, the owner provides the UCC Company Prefix and the global identification of the customer to the data store 12 together with the identities (that is, the MAC addresses in this embodiment) of the remote readers 52, 62 permitted to request authentication of the security feature 110.

The next step (step 206) is to install the readers 52, 62 into the appropriate customer facilities, that is, the manufacturing plant 50 and the distribution facility 60. This is performed by connecting the readers 52, 62 to the appropriate concentrator 54, 64.

Each reader 52, 62 may be provided with a keypad so that an operator has to enter an access code prior to the reader 52, 62 allowing the operator to access any of the reader's functions. Alternatively, a biometric input device (e.g., a fingerprint sensor), a card reader, or the like may be used to restrict access to the reader 52, 62 to one or more authorized users. For readers 52, 62 located in secure facilities, no additional access codes or permissions may be required. Additionally or alternately, a keypad, a biometric input device, a card reader or the like may be used to identify a user of a reader for association of the user with the package and/or item in a data management system as described in, for example, the fourth aspect of the invention (authentication system) disclosed hereinabove.

The next step (step 208) is to send a registration request from the readers 52, 62 to the data management system 10. This involves switching the readers 52, 62 to registration mode by a user pressing the function button 130 repeatedly until the LCD panel 128 displays "Registration". In registration mode, when the trigger 126 is pressed the reader 52, 62 verifies that the dongle 176 is present (by reading the unique code stored in the dongle and comparing it with a dongle code in the non-volatile storage 158. If the dongle 176 is present, the reader 52,62 sends an encrypted registration request to the data management system 10 via the appropriate concentrator 54, 64. The registration request includes the MAC address of the reader 52, 62 and the global identification of the customer (from the non-volatile storage 158). Where a global positioning system (GPS) unit is installed in the readers 52, 62, then GPS location information may also be transmitted.

On receipt of the registration request, reader interface 44 decrypts the request and conveys it to the secure reader authenticator 22, which parses the registration request to obtain the MAC address of the reader 52, 62 that sent the request, and the global identification of the customer. The secure reader authenticator 22 then accesses the data store 12 to authenticate the reader 52, 62 (step 210). The reader interface 44 may convey the decrypted request directly to the secure reader authenticator 22, or it may transfer the decrypted request to the non-volatile storage 30 to allow any available authenticator node $16_x$ to action the decrypted request.

To authenticate the reader 52, 62 the following authentication process is used. The secure reader authenticator 22 ascertains if the MAC address of the reader 52, 62 sending the registration request matches the MAC address of permitted readers stored in the reader identification storage node 12c. If there is a match, then the secure reader authenticator 22 then ascertains if the MAC address of the permitted reader 52, 62 is associated with the global identification of the customer. This is implemented by searching data entry 180 for that customer (based on the global identification or the UCC Company Prefix, both of which are stored in the identification information 182 of that entry 180). If the reader information 188 for that entry 180 includes a reference to a reader 52, 62 having that MAC address, then the permitted reader 52, 62 is associated with that customer.

If they are associated (that is, if the permitted reader 52, 62 is owned or operated by (or under the authority of) the customer identified by the global identification) then the secure reader authenticator 22 conveys a registration successful communication to the secure reader 52, 62. In embodiments where a GPS unit is installed in the readers 52, 62, then the GPS location information sent by the secure reader 52, 62 may also be validated by comparing it with location information stored in the reader identification storage node 12c prior to conveying a registration successful communication to the secure reader 52, 62. The registration successful communication includes the system identification 32 (FIG. 1), and a registration successful field.

If there is not a match between the received MAC address and permitted MAC addresses, or if the received MAC address is not associated with the customer that sent the registration request, then the secure reader authenticator 22 conveys a registration unsuccessful communication to the secure reader 52, 62. The registration unsuccessful communication includes the system identification 32 (FIG. 1), and a registration unsuccessful field. The secure reader authenticator 22 adds information about unsuccessful registration attempts to the log file 28.

If the reader 52, 62 is successfully registered, then the data store 12 updates its entries accordingly, using an update object from objects repository 34 (step 212). This allows that registered secure reader 52, 62 to send authentication requests.

The secure module 150 also illuminates a registered icon on the LCD panel 128 to notify a user of the reader 52, 62 that the reader 52, 62 is ready to send authentication requests (step 214).

If the reader 52, 62 is not successfully registered, then the secure reader authenticator 22 will not accept authentication requests from that secure reader 52, 62 until it has been registered. The secure module 150 also illuminates an unregistered icon on the LCD panel 128 (step 216).

If the dongle 176 is removed from the port 174, then the reader 52, 62 detects this. For example, the secure module 150 may poll the dongle 176 periodically to verify that the dongle 176 is present and that the correct code is being provided by the dongle 176. If the dongle 176 is not present, then the reader 52, 62 transmits a de-registration request to the data management system 10.

Association of Security Features with Barcodes

The second operation that will be described is association of the security feature 110 with the barcode 106. This operation will be described with reference to FIG. 8, which is a flowchart illustrating the steps involved in requesting an entry to be populated in the data store 12 for the type of microprocessor 100 being manufactured in the plant 50 and the particular optical signature of the security feature 110 that will be applied to it.

Once the 2D barcode 106 applied to the microprocessor 100 and the particular security feature 110 applied to that barcode 106 have been associated, the same security feature 110 can be routinely applied to that type of microprocessor 100 (providing that microprocessor 100 has the same 2D barcode, or at least the same UCC Company Prefix). In other words, the association of a security feature 110 with a 2D barcode only needs to occur once, and if it occurs more than once then there may be a security problem, such as a replay attack.

The first step is to change the mode of the registered manufacturing reader 52 to entry creation mode (step 220). This is performed by a user pressing the function button 130 repeatedly (thereby toggling through different modes) until the LCD panel 128 displays "New Entry". If the manufacturing reader 52 is not registered, then the reader 52 will not change to entry creation mode. In this embodiment, the readers 62 in the distribution facility are not equipped with entry creation mode.

Once in entry creation mode, the user scans the 2D barcode 106 on the microprocessor 100 by aligning the scanning window 120 with the barcode 106 and depressing the trigger 126 (step 222). This causes the 2D barcode imager 122 and associated control electronics 124 to scan and decode the barcode 106, and the read engine 140 and security module 150 to read and decode the security feature 110.

In entry creation mode, the security module 150 uses default interrogation parameters 170 stored in the non-volatile storage 158 and executed by the control electronics 154. The interrogation parameters 170 relate to how long the LEDs 144 are energized, whether the spectrometer 142 records luminescence while the LEDs 144 are energized or a preset time delay after the LEDs 144 are de-energized, and such like.

Once the barcode 106 and security feature 110 have been read, the security module 150 then creates an association request (step 224). An association request informs the data store 12 about data from a security feature and data from an item tagged by that security feature. In this embodiment, the item is the microprocessor 100 and the data from a security feature 110 (which is lanthanide-doped silica particles suspended in an optically transparent ink) is the spectral signature of the security feature 110.

Figure 9A:
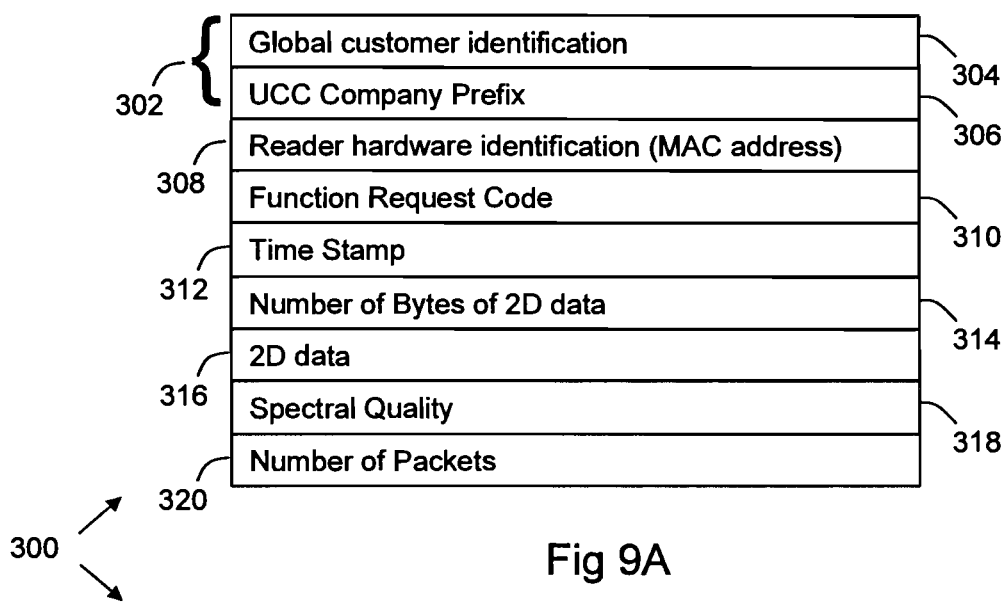
FIG. 9A is a diagram illustrating the format of an association request packet sent from the secure reader of FIG. 3 to the data management system of FIG. 1.
Figure 9B:
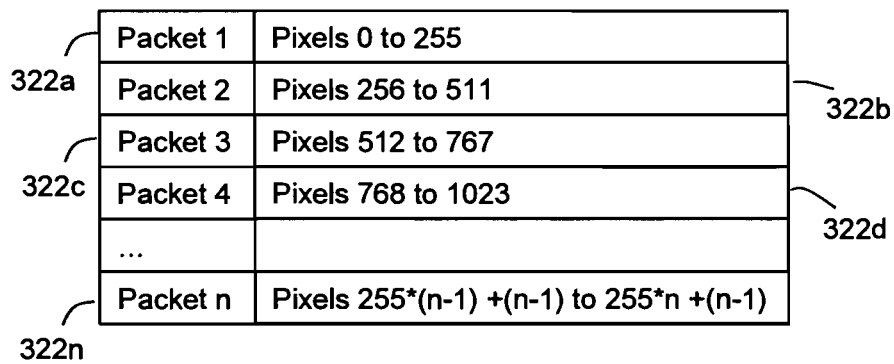
FIG. 9B is a diagram illustrating the format of association data packets sent with an association request packet from the secure reader of FIG. 3 to the data management system of FIG. 1.

To create the association request, the security module 150 constructs a request packet and data packets having the formats shown in FIGS. 9A and 9B respectively. The association request 300 comprises: customer identification information 302 (in FIG. 9A this is provided by a global customer identification field 304 and a UCC Company Prefix field 306), reader identification information 308 (in the form of a MAC address), function request information 310 (in the form of a code indicating that the request is an association request), timestamp information 312 (generated by the timestamp generator 168 in the control electronics 154), barcode data size information 314 indicating the number of bytes of 2D barcode data that will be included in the association request 300, barcode data 316 (obtained during the scanning step 222), spectral quality information 318 indicating the number of pixels covered by each data packet, packet number information 320 indicating the number of data packets to follow, and actual data packets 322a to 322n corresponding to the packet number information 320. The actual data packets may be transmitted separately from fields 302 to 320 for more efficient communication.

The actual data packets 322 contain the security feature spectral information read during the scanning step 222. This information will be stored in the data store entry for the item having the 2D barcode identified by the barcode data field 316 (in this example, the microprocessor 100). In this embodiment, each data packet 322 contains 256 pixels, and there are sixteen data packets, which results in 4096 pixels for the security feature spectrum.

Once the security module 150 has populated the association request 300 with the relevant data, the next step is for the security module 150 to encrypt and transmit the association request 300 to the reader interface 44 in the port 40 of the data management system 10 (step 226).

On receipt of this encrypted association request, the reader interface 44 decrypts the request 300 (step 228). If the association request 300 cannot be decrypted then the reader interface 44 responds to the remote reader 52 with a failure message (step 234), and updates the log file 28 with details of the failed request. If the association request 300 is correctly decrypted, then the interface reader 44 conveys the decrypted association request 300 to the secure reader authenticator 22 (step 230).

Figure 7:
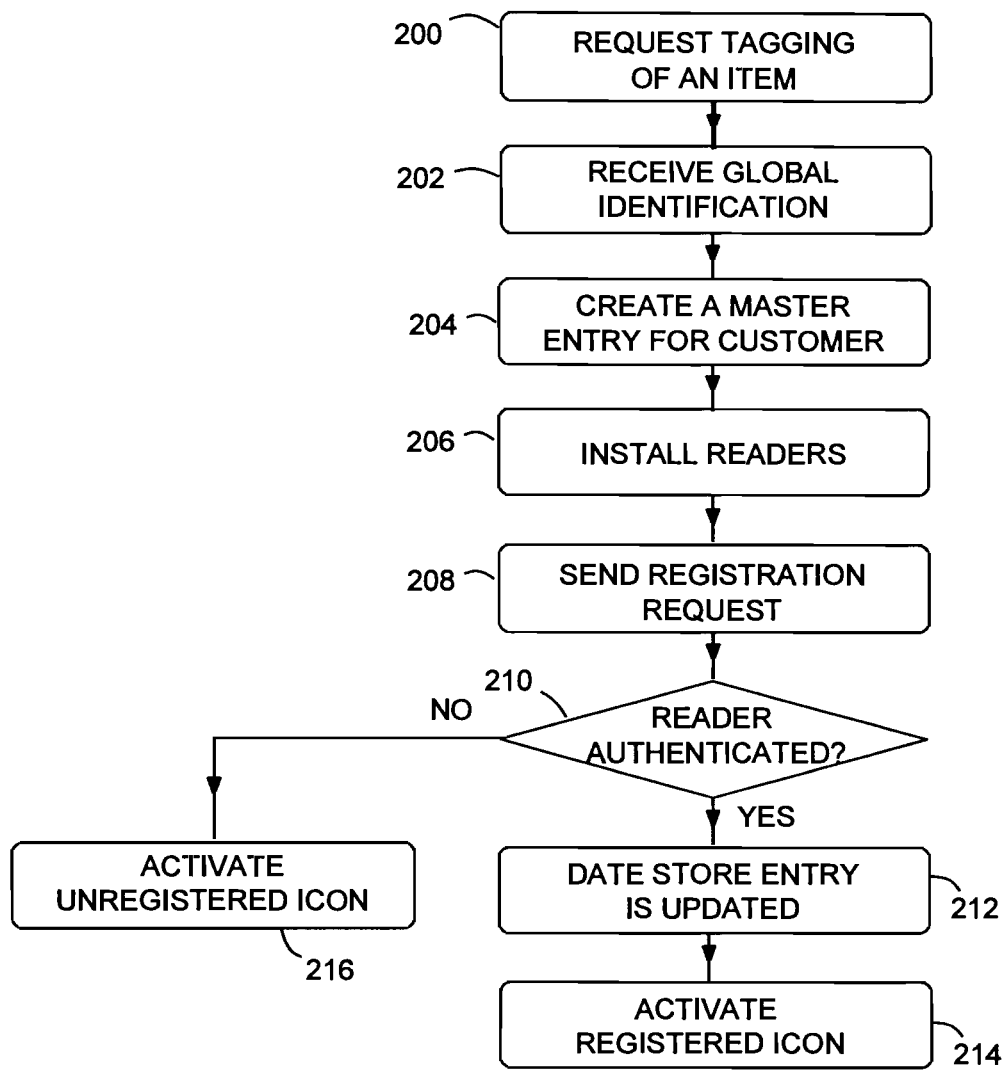
FIG. 7 is a flowchart illustrating the steps involved in registering a secure reader of FIG. 3 with the data management system of FIG. 1.

The secure reader authenticator 22 parses the association request 300 to authenticate the reader 52 (step 232) that sent the message in a similar way to that described with reference to step 210 of FIG. 7; namely, the secure reader authenticator 22 ascertains if the MAC address corresponds to that of a permitted registered reader 52, and if so, if the permitted registered reader 52 is owned or operated by (or under the authority of) the customer (that is, if the global identification in the request 300 matches that associated with the reader 52 in the reader identification storage node 12c).

If the reader authentication step (step 232) is not successful, then the secure reader authenticator 22 conveys a failure message to the security module 150 via the reader interface 44 and the concentrator 54 (step 234), and updates the log file 28 with details of the failed request. The failure message includes the unique system identification 32 and a failure field that indicates that the association request 300 was not successful.

If the reader authentication step (step 232) is successful, then the secure reader authenticator 22 creates a new entry in the data store 12 under the master entry 180 for that customer (step 236) using an entry creation object from the object repository 34. The new entry includes the optical spectrum information contained in the data packets 322 (stored in the security feature information 186), in addition to the barcode information 316 (which is stored in the item information 184), part of which is the UCC Company Prefix 306 (which is also stored separately in the identification information 182). The data store 12 may include additional fields, such as the timestamp information 312, a hash of the 2D barcode information 316, and a transformation of the optical spectrum information from the data packets 322.

Authentication of Items (the Microprocessor)

Once a data store entry has been created for the particular security feature 110 (that is, the optical luminescence spectrum emitted by the security feature 110 in response to excitation) applied to the microprocessor 100, that type of microprocessor 100 (that is, that model of microprocessor manufactured by the customer in the manufacturing plant 50) can be subsequently authenticated as it travels through the distribution chain.

To confirm that the security feature 110 is working correctly and/or applied correctly, one in every batch of microprocessors 100 (for example one in a hundred or one in a thousand microprocessors 100) manufactured may be authenticated at the manufacturing plant 50 prior to shipping to the distribution facility 60.

Figure 10:
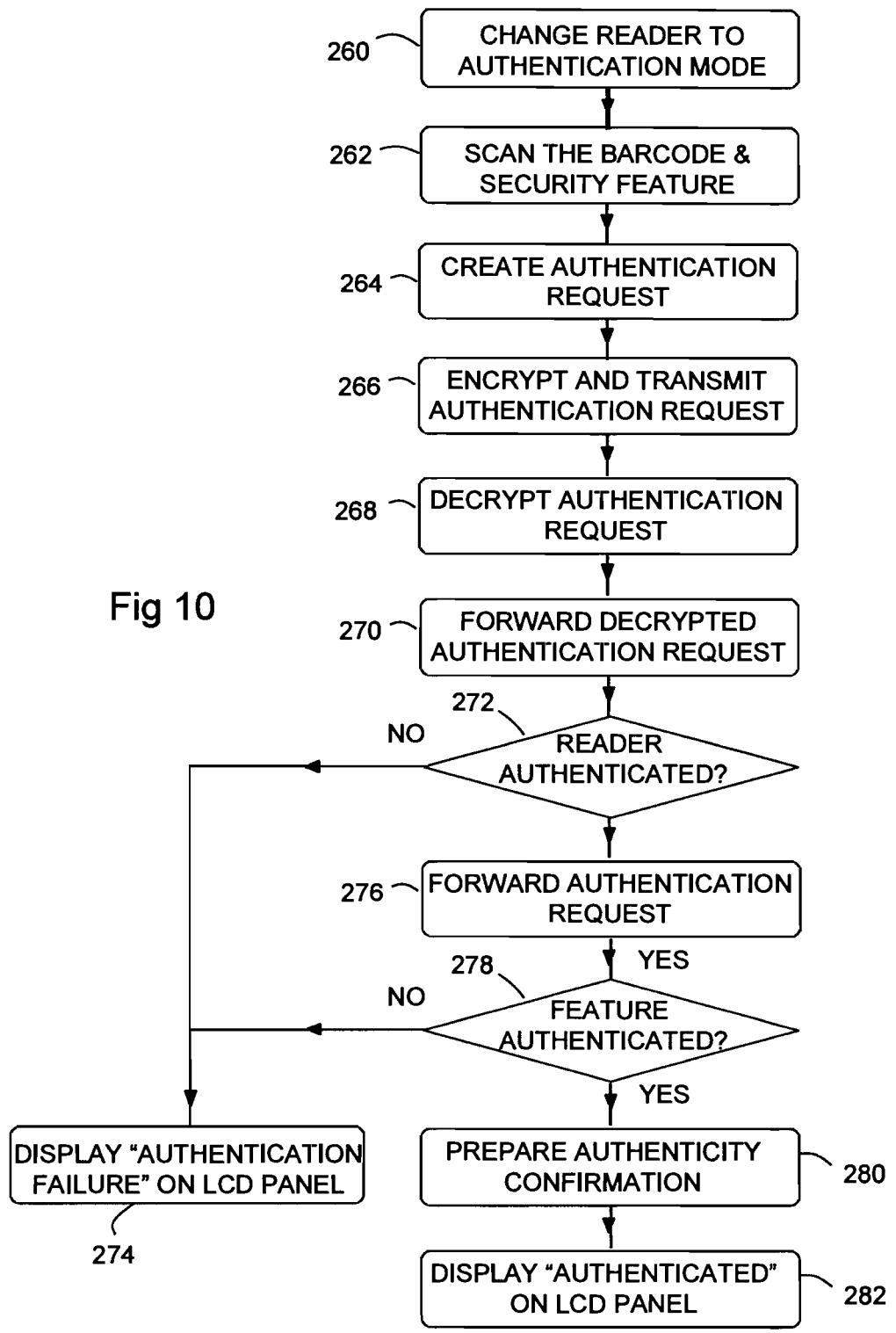
FIG. 10 is a flowchart illustrating the steps involved in authenticating an item (a microprocessor) using the data management system of FIG. 1.

On arrival at the distribution facility 60, one in every batch of microprocessors 100 received may be authenticated to validate that the microprocessors 100 are genuine. The authentication process is the same, whether performed at the manufacturing plant 50 or the distribution facility 60, and will now be described with reference to FIG. 10, which is a flowchart illustrating the steps involved in authenticating an item (the microprocessor 100) using the data management system of FIG. 1.

The first step in the authentication process is to change the registered manufacturing or distribution reader 52, 62 to authentication mode (step 260). This is performed by a user pressing the function button 130 repeatedly (thereby toggling through different modes) until the LCD panel 128 displays "Authentication". If the reader 52, 62 is not registered, then the reader 52, 62 will not change to authentication mode.

Once in authentication mode, the user scans the 2D barcode 106 on the microprocessor 100 by aligning the scanning window 120 with the barcode 106 and depressing the trigger 126 (step 262). This causes the 2D barcode imager 122 and associated control electronics 124 to scan and decode the barcode 106, and the read engine 140 and security module 150 to read and decode the security feature 110.

In this embodiment, in authentication mode, the security module 150 uses default interrogation parameters 170 stored in the non-volatile storage 158. The interrogation parameters relate to how long the LEDs 144 are energized, whether the spectrometer 142 records luminescence while the LEDs 144 are energized or a preset time delay after the LEDs 144 are de-energized, and such like.

Once the barcode 106 and security feature 110 have been read, the security module 150 then creates an authentication request (step 264). An authentication request conveys data from the security feature 110 to the data store 12. In this embodiment, the item is the microprocessor 100 and the data from the security feature 110 (which is lanthanide-doped silica particles suspended in an optically transparent ink) is the spectral signature of the security feature 110.

Figure 11:
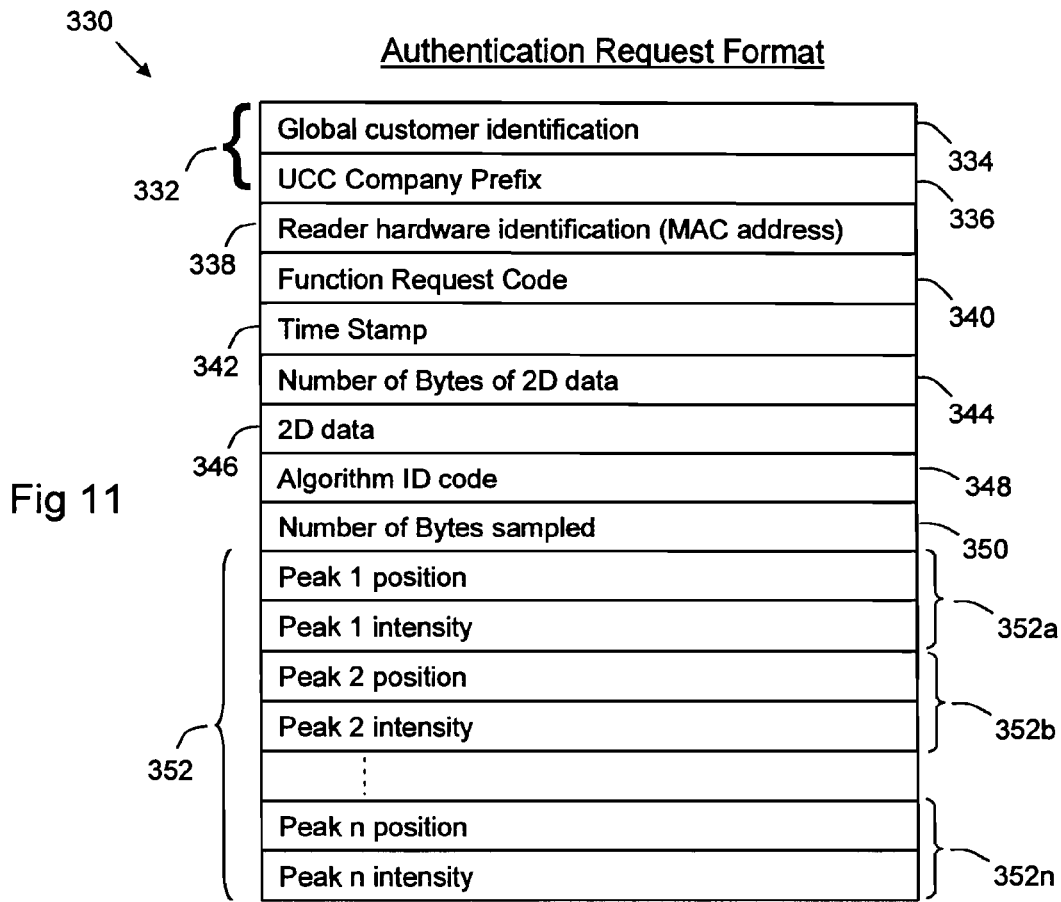
FIG. 11 is a diagram illustrating the format of an authentication request sent from the secure reader of FIG. 3 to the data management system of FIG. 1.

To create the authentication request, the security module 150 constructs a request packet having the format shown in FIG. 11. The authentication request 330 comprises: customer identification information 332 (provided by a global customer identification field 334 and a UCC Company Prefix field 336), reader identification information 338 (in the form of a MAC address), function request information 340 (in the form of a code indicating that the request is an authentication request 330), timestamp information 342 (generated by the timestamp generator 168 in the control electronics 154), barcode data size information 344 indicating the number of bytes of 2D barcode data that will be included in the authentication request 330, barcode data 346 (obtained during the scanning step 262), an algorithm identification code 348 (which identifies the specific algorithm 172 that was used to read the security feature 110), a sample size field 350 that indicates the number of bytes sampled (that is, the number of pairs of fields to follow), and pairs of data points fields 352a, b, . . . n. Each pair of fields 352 containing a peak position and its associated intensity, with the number of data points fields 352 being indicated by the sample size field 350. The pairs of data points fields 352 may be transmitted with fields 334 to 350, or may be transmitted separately from fields 334 to 350 for more efficient communication.

The pairs of data points fields 352 contain portions of, or derived from, the security feature spectral information read during the scanning step 262.

Once the security module 150 has populated the authentication request 330 with the relevant data, the next step is for the security module 150 to encrypt and transmit the authentication request 330 to the reader interface 44 in the port 40 of the data management system 10 (step 266).

On receipt of this encrypted authentication request, the reader interface 44 decrypts the request 330 (step 268). If the authentication request 330 cannot be decrypted then the reader interface 44 responds to the remote reader 52, 62 with a failure message, and updates the log file 28 with details of the failed request. If the authentication request 330 is correctly decrypted, then the interface reader 44 conveys the decrypted authentication request 330 to the secure reader authenticator 22 (step 270).

The secure reader authenticator 22 parses the authentication request 330 to authenticate the reader 52, 62 (step 272) that sent the message in a similar way to that described with reference to step 210 of FIG. 7; namely, the secure reader authenticator 22 ascertains if the MAC address corresponds to that of a permitted registered reader 52, 62, and if so, if the permitted registered reader 52, 62 is owned or operated by (or under the authority of) the customer (that is, if the global identification in the request 330 matches that associated with the reader 52, 62 in the reader identification storage node 12c).

If the reader authentication step (step 272) is not successful (for example, because the MAC is not present, or present but not correct, or because the global identification in the request is not a recognized global identification, or because it is a recognized global identification but does not correspond to the global identification associated with that MAC address), then the secure reader authenticator 22 conveys a failure message to the security module 150 via the reader interface 44 and the appropriate concentrator 54, 64 and updates the log file 28 with details of the failed request. The failure message includes the unique system identification 32 and a failure field that indicates that the authentication request was not successful. On receipt of a failure message from the data management system 10, the reader 52, 62 displays "Authentication Failure" on the LCD panel 128 (step 274).

If the reader authentication step (step 272) is successful, then the secure reader authenticator 22 conveys the authentication request 330 to the security feature authenticator 20 (step 276).

Figure 8:
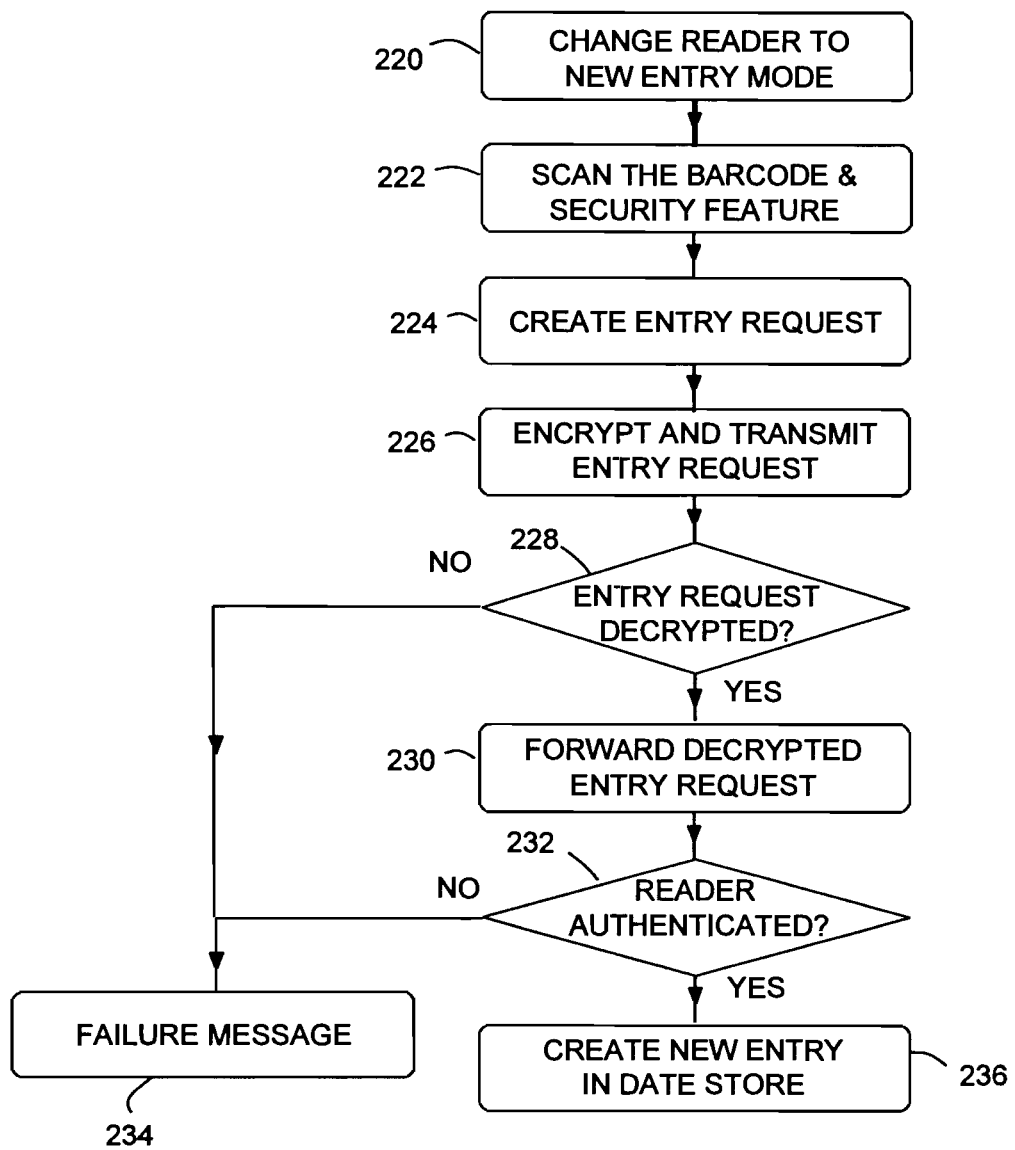
FIG. 8 is a flowchart illustrating the steps involved in populating an entry in the data management system of FIG. 1 that associates a security feature with a spatial code.

The security feature authenticator 20 parses the authentication request 330 to ascertain the algorithm identification code 348 and the pairs of data points fields 352a, b, . . . n. The security feature authenticator 20 reviews the algorithm identification code 348 to ascertain if the optical spectrum information contained in the security feature information 188 needs to be transformed prior to comparing this information with the information from the pairs of data points fields 352. The optical spectrum information contained in the security feature information 188 was populated during step 236 (FIG. 8).

If the optical spectrum information needs to be transformed, then the security feature authenticator 20 first accesses a pre-stored algorithm (referenced by the algorithm identification code 348) to implement the required transformation. If the optical spectrum information does not need to be transformed, then the security feature authenticator 20 compares the information from the pairs of data points fields 352 with the optical spectrum information contained in the security feature information 188 (step 278).

If the feature authentication step (step 278) is not successful, then the security feature authenticator 20 conveys a failure message to the security module 150 via the reader interface 44 and the appropriate concentrator 54, 64 and updates the log file 28 with details of the failed request. The failure message includes the unique system identification 32 and a failure field that indicates that the authentication request was not successful.

On receipt of a failure message from the data management system 10, the reader 52, 62 validates that the unique system identification 32 corresponds to that stored in the non-volatile storage 158, and if so, displays "Authentication Failure" on the LCD panel 128 (step 274). If the unique system identification 32 does not correspond to that stored in the non-volatile storage 158, then the reader 52, 62 displays an error message, which may indicate an attempted man-in-the-middle attack on the authentication system 8.

If the feature authentication step (step 278) is successful, then the security feature authenticator 20 updates the entry 180 (using the update object from object repository 34) to include the identity of the reader 52, 62 that requested authentication, the timestamp from field 342, and any other desired information. The security feature authenticator 20 also prepares an authenticity confirmation for sending to the reader 52, 62 that sent the authentication request 330 (step 280).

Figure 12:
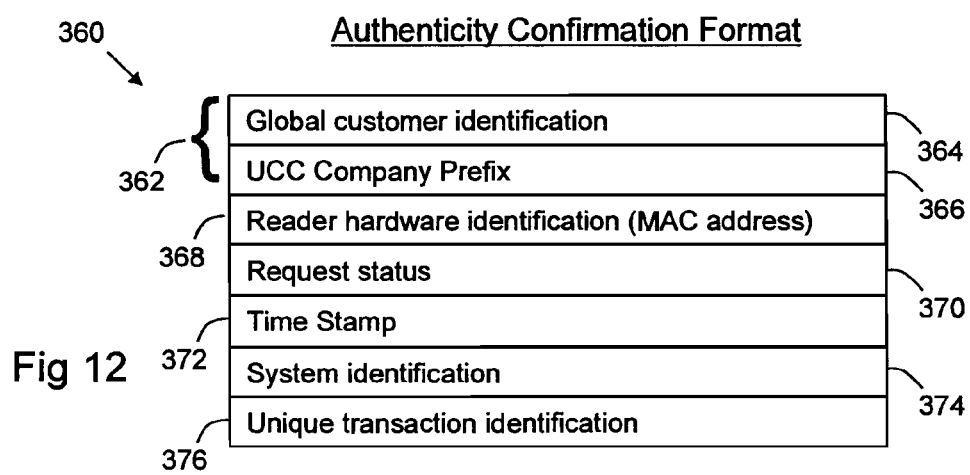
FIG. 12 is a diagram illustrating the format of an authenticity confirmation sent from the data management system of FIG. 1 to the secure reader of FIG. 3.

The authenticity confirmation has the format shown in FIG. 12. The authenticity confirmation 360 comprises: customer identification information 362 (provided by a global customer identification field 364 and a UCC Company Prefix field 366), reader identification information 368 (in the form of a MAC address), request status information 370 (which is set to indicate that the authentication request was successful), timestamp information 372 (generated by the timestamp generator 26), a system identification field 374 populated by the unique system identification 32 from the shared resources 18, and a unique transaction identifier field 376 populated by the current value of the transaction identifier counter 36.

The security feature authenticator 20 then sends the authenticity confirmation 360 to the reader 52, 62 via the reader interface 44 and the appropriate concentrator 54, 64.

On receipt of the authenticity confirmation 360, the reader 52, 62 parses the authenticity confirmation 360 to validate that the system identification 32 corresponds to that stored in the non-volatile storage 158, and then displays "Authenticated" on the LCD panel 128 (step 282). If the system identification 32 does not correspond to that stored in the non-volatile storage 158, then the reader 52, 62 displays an error message.

The reader 52, 62 then stores the timestamp value from field 372 and the transaction identifier from field 376 in non-volatile storage 158, thereby over-writing any previously stored timestamp value and transaction identifier.

Any subsequent authentication request 330 will only be accepted by the reader authenticator 22 if the timestamp of the subsequent request is greater than that of the last stored timestamp.

Similarly, any subsequent authenticity confirmation 360 will only be treated as authentic by a reader 52, 62 if the authenticity confirmation 360 has a transaction identifier that is greater than the last stored transaction identifier, and a timestamp that is greater than the last stored timestamp.

The reader authenticator 22 and the security feature authenticator 20 may be operable to trigger an exception process in the event that any authentication step is not successful. The exception process may activate a notification object from the object repository 34 to notify the owner and/or the customer about the unsuccessful attempt to authenticate an item, register a reader, or to populate an entry.

On each occasion that an item (such as the microprocessor 100) is successfully validated, the data management system 10 may update the data store 12 with details of the time at which the authentication occurred, the reader identity and location that issued the authentication request, and any other desired information. In this example, storage node 12d is used to store this information, and there is a link in the reader information 188 to this storage node 12d.

Control of the Remote Readers 52, 62

The fourth operation of the networked security system that will be described is control of the remote readers 52, 62. For an additional fee, the owner of the data management system 10 may transfer reading configuration parameters to the remote readers 52, 62 to instruct the remote readers 52, 62 about how to interrogate the security feature 110 and/or process the optical response from the security feature 110. To implement this, the data management system 10 can periodically (for example, daily, weekly, or monthly) supply the security modules 152 with a reader control command containing new information for the interrogation parameters 170 and the processing algorithms 172 in the non-volatile storage 158. Issuance of the reader control command may be triggered by a parameter issuing object from the object repository 34.

Figure 13:
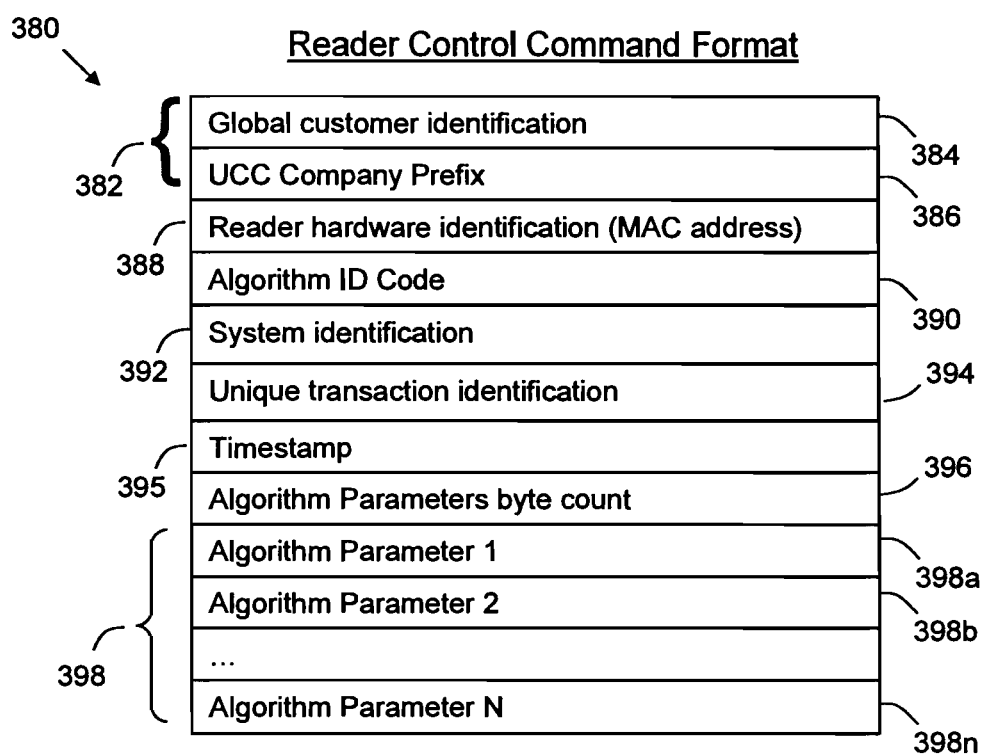
FIG. 13 is a diagram illustrating the format of a reader control command sent from the data management system of FIG. 1 to the secure reader of FIG. 3.

FIG. 13 illustrates the format of the reader control command 380, which comprises: customer identification information 382 (provided by the global customer identification field 384 and the UCC Company Prefix field 386), reader identification information 388 (in the form of a MAC address), an algorithm identification code 390 (which identifies the specific algorithm 172 that should be used by the reader 52, 62 to read the security feature 110, a system identification field 392 populated by the unique system identification 32 from the shared resources 18, a unique transaction identifier field 394 populated by the current value of the transaction identifier counter 36, timestamp information 395 (generated by the timestamp generator 26), a parameters byte count 396 indicating the number of algorithm parameters contained within the reader control command 380, and algorithm parameters fields 398a, b, . . . n.

The algorithm parameters fields 398 contain the actual parameters that will be used by the control electronics 154 to interrogate a security feature 110 and to process the response detected from the security feature 110. For interrogation of a security feature 110, these parameters may control: the type of excitation (where multiple different LEDs are available to choose from), duration of excitation, any time delay between ceasing excitation and measuring luminescence. For processing the luminescence measured from the security feature 110, these parameters may also control: whether the raw wavelength and corresponding intensity information is conveyed to the data management system 10, whether only the peaks are conveyed, whether only certain points (whether peaks or not) are conveyed, whether a transformation is applied to the raw wavelength and corresponding intensity information, and such like.

When a reader 52, 62 receives a reader control command 380, the reader 52, 62 first validates that the unique system identification 32 from the system identification field 392 corresponds to that stored in the non-volatile storage 158, and that the identifier in the unique transaction identifier field 394 and the timestamp information 395 are both greater than the last transaction identification and timestamp stored, respectively. If these are all validated, then the reader 52, 62 updates its non-volatile storage 158 to include the new parameters. All subsequent attempts by the reader 52, 62 to read the security feature 110 will use these newly-provided parameters.

It will now be appreciated that the requests and command 300, 330, 360, and 380 contain many fields that are identical. For example, the global customer identification fields 304, 334, 364, and 384 are all the same.

If the customer desires to receive information about how many times the microprocessors 100 have been authenticated, how many unsuccessful authentication attempts have been made, and such like, then the customer can access the query database 11b from the customer's headquarters 70 using a computer system 72. The query database 11b contains a copy of the information stored in the data store 12 (as updated periodically).

The customer has password-protected access to a limited number of queries. One of these queries is to download the log file 28 for one or more of the customer's items (for example, the microprocessor 100) using the customer's global identification or UCC Company Prefix. Another query is to trace one of the customer's items (for example, the microprocessor 100). This provides the customer with a track and trace solution for the customer's items.

It will also be appreciated that this embodiment allows the owner, and other parties authorized by the owner, for example a distributor, to authenticate a microprocessor 100 using a secure reader 52, 62.

The algorithms and parameters used to interrogate the security feature 110 and process the luminescence detected are all stored in non-volatile storage 158 that is automatically erased if an attempt is made to access it by breaking into the security module 150.

The system also retains a log file 28 of unsuccessful attempts to authenticate an item, such as the microprocessor 100.

Another embodiment of the present invention will now be described with reference to FIGS. 14 to 16.

Figure 14:
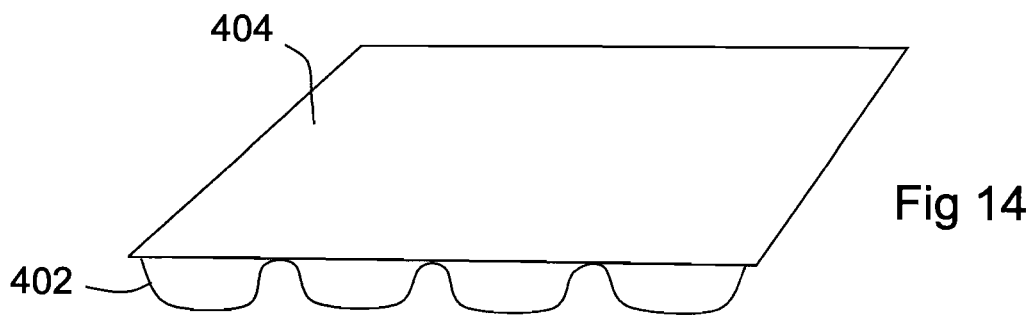
FIG. 14 is a perspective drawing of a package according to another embodiment of the present invention.

In FIG. 14, a blister package 400 is shown as a perspective view. The package 400 comprises an optically transparent plastic base 402, conforming to FDA requirements for plastics used to package pharmaceuticals, sealed by a foil cover 404.

Figure 15:
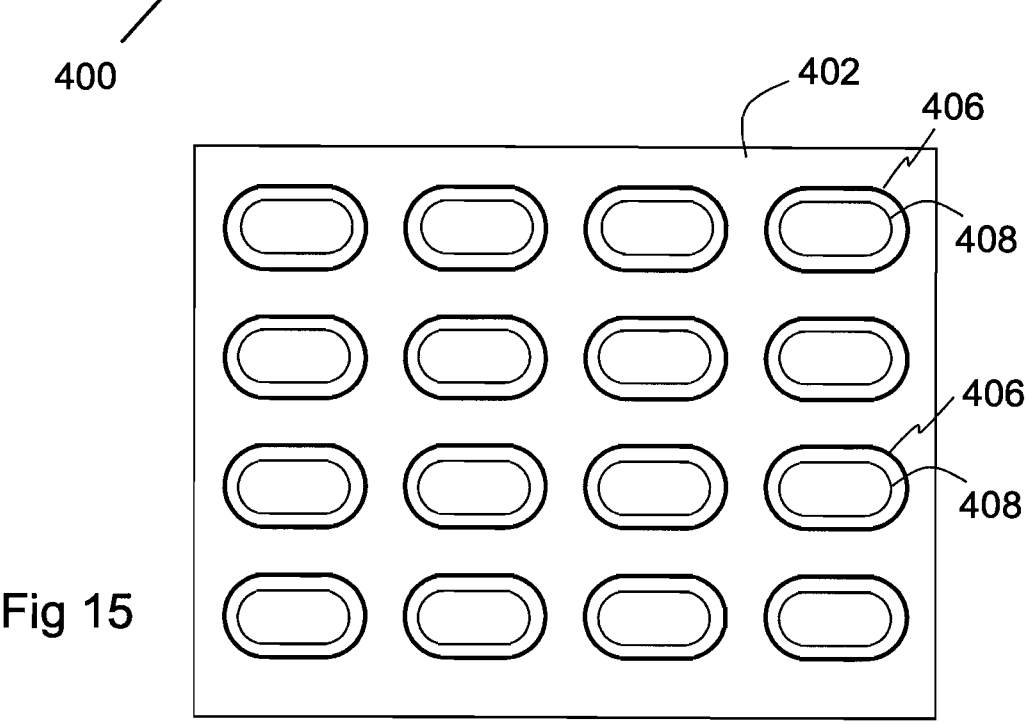
FIG. 15 is an underside plan view of the package of FIG. 14.

As best seen in FIG. 15, the base 402 comprises a plurality of individual pharmaceutical compartments 406 (sixteen are illustrated in FIG. 15, although only two of these compartments 406 are labelled). Each compartment 406 contains a pharmaceutical 408 (an item) to which the compartment 406 has been conformably molded.

Figure 16:
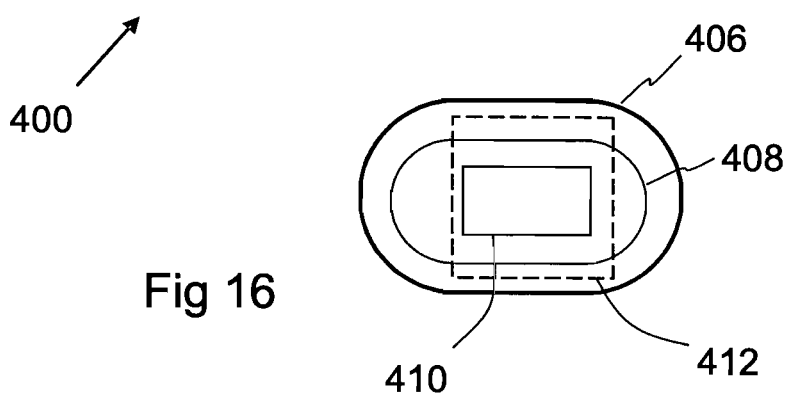
FIG. 16 is an enlarged view of a portion of the package of FIGS. 14 and 15.

As best seen in FIG. 16, which shows one compartment 406 greatly enlarged. The pharmaceutical 408 includes a coating on which an item code 410 can be laser written using, for example, the Pharmamark (trade mark) coating available from DataLase (trade mark) which has been approved for use in ingestibles by the FDA.

The item code 410 is a 2D barcode that is written using a low power carbon dioxide laser. In registration with the item code 410 is a security code 412 that is not visible to the human eye. The security code 412 is a luminophore that luminesces in the IR range of the electromagnetic spectrum. In this embodiment, there is a unique security code in registration with each unique item code.

In use, a reader, such as reader 52, can be used to read both the item code 410 and the security code 412. In a similar way to the above embodiments, when the package 400 is manufactured, each compartment 406 is scanned by the reader 52, and a data store records the association between the item code 410 and the security code 412. To validate the package 400, a potential consumer of the pharmaceuticals 408, or a distributor of the pharmaceuticals, can scan a compartment 406 using the reader 52 to ensure that the pharmaceutical item code 410 matches the security code 412. Such readers 52 may be located within kiosks or on counters in retail outlets, such as pharmacies.

Various modifications may be made to the above described embodiments within the scope of the present invention. For example, the data store may only have a single storage node. The architecture of the data store is not critical to these embodiments of the invention, and any convenient data store architecture may be employed.

In other embodiments, only one authenticator node may be used. Where multiple authenticator nodes are used, the shared resources 18 may be implemented by each authenticator node, so that there are multiple shared resources 18. Where only one authenticator node is used, a load balancer may not be required, nor the storage in the shared resources.

In other embodiments, the security feature may not be based on optical properties, for example, an RFID security feature may be used. In other embodiments, a security feature based on optical properties (such as a hologram) may be used. In other embodiments that are based on luminescence, the security feature may be a luminophore comprising a silica matrix. The silica matrix may enclose a dye, quantum dots, or any other convenient luminescing substance.

In the above embodiment, the remote secure readers include a unique hardware identification implemented using a MAC address on a communications adapter in the readers. In other embodiments, the unique identification may not be based on a hardware component, and/or it may be located in the security module of the reader.

In the above embodiment, the UCC Company Prefix was used as the index to the data store, which enabled a barcode to be scanned and used as an index to access the correct entry 180. In other embodiments, for example where barcodes are not used, the global customer identification may be stored in the remote readers and conveyed to the data management system each time an entry is to be populated.

In other embodiments, the owner may populate all data entries.

In other embodiments, the secure readers may not have to be registered prior to sending authentication requests. In other embodiments, each customer may have only one security feature (that is, only one optical signature), so an association request may not be required. Association requests are advantageous where the customer decides which of a plurality of optical signatures assigned to the customer by the owner should be associated with which product.

In other embodiments, the networked authentication system 8 may be implemented as a closed system within a company (for example, using an intranet), so the secure readers may not require the high level of security described in the above embodiment. In such embodiments, the readers may have little or no security.

In the above embodiment, the readers 52, 62 convey to the data store the peak positions of the luminescence spectrum derived from the security feature 110; in other embodiments, the readers 52, 62 may convey the entire spectrum, or a transformation of parts of, or all of, the spectrum. If the entire spectrum is to be transmitted, the intensity values may be transmitted together with information about the starting wavelength, the ending wavelength, and the wavelength step between points. Any other convenient format may be used for transmitting the intensity and wavelength data.

In the above embodiment, the LCD panel 128 only displays limited information. In other embodiments, the authenticity confirmation may include details of the item (the microprocessor 100 in the above embodiment) from the item information field 184, so that these details can be displayed on the LCD panel 128.

In other embodiments, an authenticity confirmation may be in the form of a certificate of authenticity that can be transmitted to and automatically processed by other computer systems.

In the above embodiment, different barcodes having the same UCC Company Prefix had the same entry in the data store 12; whereas, in other embodiments, any difference in barcodes may require a different entry in the data store 12.

In other embodiments, the 2D barcode information received in an authentication request 330 may be hashed by the secure reader authenticator 22 and compared with a hash of the 2D barcode stored in the item information 184. An authenticity confirmation 360 may not be issued unless the two hashes match. This ensures that the 2D barcode on the item being authenticated must match the 2D barcode recorded in the data store for that item.

In other embodiments, spatial codes other than 2D barcodes may be used, such as conventional UPC barcodes or proprietary codes.

In the above embodiment, one in every batch of microprocessors 100 is authenticated at the manufacturing plant 50 and at the distribution facility 60; in other embodiments, microprocessors 100 may only be authenticated at a final destination or if returned as faulty to the manufacturer.

In the above embodiment, a separate query database 11b is provided that is only periodically coupled to the data store 12; in other embodiments, the transaction database 11a may perform the functions of the query database 11b, and the customer interface 42 may be coupled to port 40.

In the above embodiment, specific data fields and data formats are provided. These, as well as other features of the embodiment, are given only by way of example to aid the skilled person in implementing an embodiment. As will be evident to one of ordinary skill in this art, numerous changes may be made to these data fields and data formats within the scope of the present invention.

In the above embodiment, an auxiliary cryptographic device was removably coupled to the secure module 150; in other embodiments, the secure module may include this functionality in an internal non-removable device, or it may not use this functionality.

What is claimed is:

1. A method of marking an item to allow validation and tracing of that item, the method comprising: providing a package having an optically transparent base defining a plurality of compartments; inserting individual items into each of the compartments; writing a unique item code on each item as a unique serial number and associating a security code with each item and each compartment, the unique item code and the security code capable of being read simultaneously by a reader, wherein the reader includes a reader identity authorizing the reader to request authentication of each unique item code and each associated security code; and applying the unique security code in registration with each compartment, to allow association of the item code and the security code for each compartment, and including for each item code a place of manufacture for the item to which it relates, each compartment including covert ink to represent each security code on that compartment as an invisible barcode adapted, via the covert ink, to be visible via photoluminescence in the near infra-red region of the electromagnetic spectrum, wherein applying further includes applying at least one unique item code to a particular item after enclosed in the package by using a low power carbon dioxide laser to write through a base material of the base onto the particular item.

2. A method according to claim 1, wherein the step of applying a security code in registration with each compartment includes applying the security code to the base.

3. A method according to claim 1, wherein the step of applying a unique security code in registration with each compartment includes applying the unique security code to a cover enclosing the base.

* * * * *